(12) United States Patent
Simons et al.

(10) Patent No.: US 6,815,187 B1
(45) Date of Patent: Nov. 9, 2004

(54) STIMULATION OF ANGIOGENESIS VIA SYNDECAN-4 CYTOPLASMIC DOMAIN SIGNALING PATHWAY

(75) Inventors: Michael Simons, Chestnut Hill, MA (US); Arie Horowitz, Waltham, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/190,976

(22) Filed: Nov. 12, 1998

Related U.S. Application Data

(60) Provisional application No. 60/073,711, filed on Feb. 4, 1998.

(51) Int. Cl.[7] ............................ C12N 9/12; A01N 61/00
(52) U.S. Cl. ............................................ 435/194; 514/1
(58) Field of Search ............................... 435/194; 514/1

(56) References Cited

U.S. PATENT DOCUMENTS 6,015,892 A * 1/2000 Bennett et al. ............ 536/24.5

OTHER PUBLICATIONS

Samokhin et al., "Effects of Protein Kinase C Inhibitors on Thromboxane Production by Thrombin–Stimulated Platelets", Eur. J. Pharmacol., 386(2/3), pp. 297–303, Dec. 1999.*
Calbiochem, On–line Catalog, Cat. No. 365250, "Gö 6976", at http://www.calbiochem.com, accessed Feb. 25, 2002.*
Harrington et al., "Enhancement of Migration by Protein Kinase C alpha and Inhibition of Proliferation and Cell Cycle Progression by Protein Kinase C delta in Capillary Endothelial Cells", J. Biol. Chem., 272(11), pp. 7390–7397, Mar. 1997.*
Gschwendt et al., "Rottlerin, A Novel Protein Kinase Inhibitor", Biochem. Biophys. Res. Comm., 199(1), pp. 93–98, Feb. 1994.*
Bronson et al., "Virtual Kinetics: Using Statistical Experimental Design for Rapid Analysis of Enzyme Inhibitor Mechanisms", Biochem. Pharm., 50(6), pp. 823–831, Sep. 1995.*
Nishikawa et al., "Determination of the Specific Substrate Sequence Motifs of Protein Kinase C Isozymes", J. Biol. Chem., 272(2), pp. 952–960, Jan. 1997.*
Mandal et al., "Interleukin–1–Induced Ether–Linked Diglycerides Inhibit Calcium–Insenstive Protein Kinase C Isotypes", J. Biol. Chem., 272(32), pp. 20306–20311, Aug. 1997.*
Keenan et al., "Isoform Specificity of Activators and Inhibitors of Protein Kinase C gamma and delta", FEBS Lett., 415(1), pp. 101–108, Sep. 1997.*
Endo et al., "Synthesis, Computer Modeling and Biological Evaluation of Novel Protein Kinase C Agonists Based on a 7–Membered Lactam Moiety", Bioorg. Med. Chem.Lett., 9(2), pp. 173–178, Jan. 1999.*
Shizukada et al., "Vascular Endothelial Growth Factor–Induced Endothelial Cell Migration and Proliferation Depend on a Nitric Oxide–Mediated Decrease in Protein Kinase C delta Activity", Circ. Res., 85(3), pp. 247–256, Aug. 1999.*

* cited by examiner

*Primary Examiner*—Jon P. Weber
(74) *Attorney, Agent, or Firm*—David Prashker

(57) ABSTRACT

The present invention provides a methodology and compositions for stimulating angiogenesis in-situ within viable cells, tissues and organs comprising endothelial cells. The methodology focuses upon and controls the phosphorylation of the 183rd amino acid residue, serine, within the cytoplasmic domain and intracellular tail of transmembrane syndecan-4 proteoglycans which are then positioned at and through the cellular membrane of viable endothelial cells. By intervening and maintaining the 183rd residue in a non-phosphorylated state, a consequential cascade of intracellular events is initiated which result in a stimulation of angiogenesis in-situ.

2 Claims, 8 Drawing Sheets

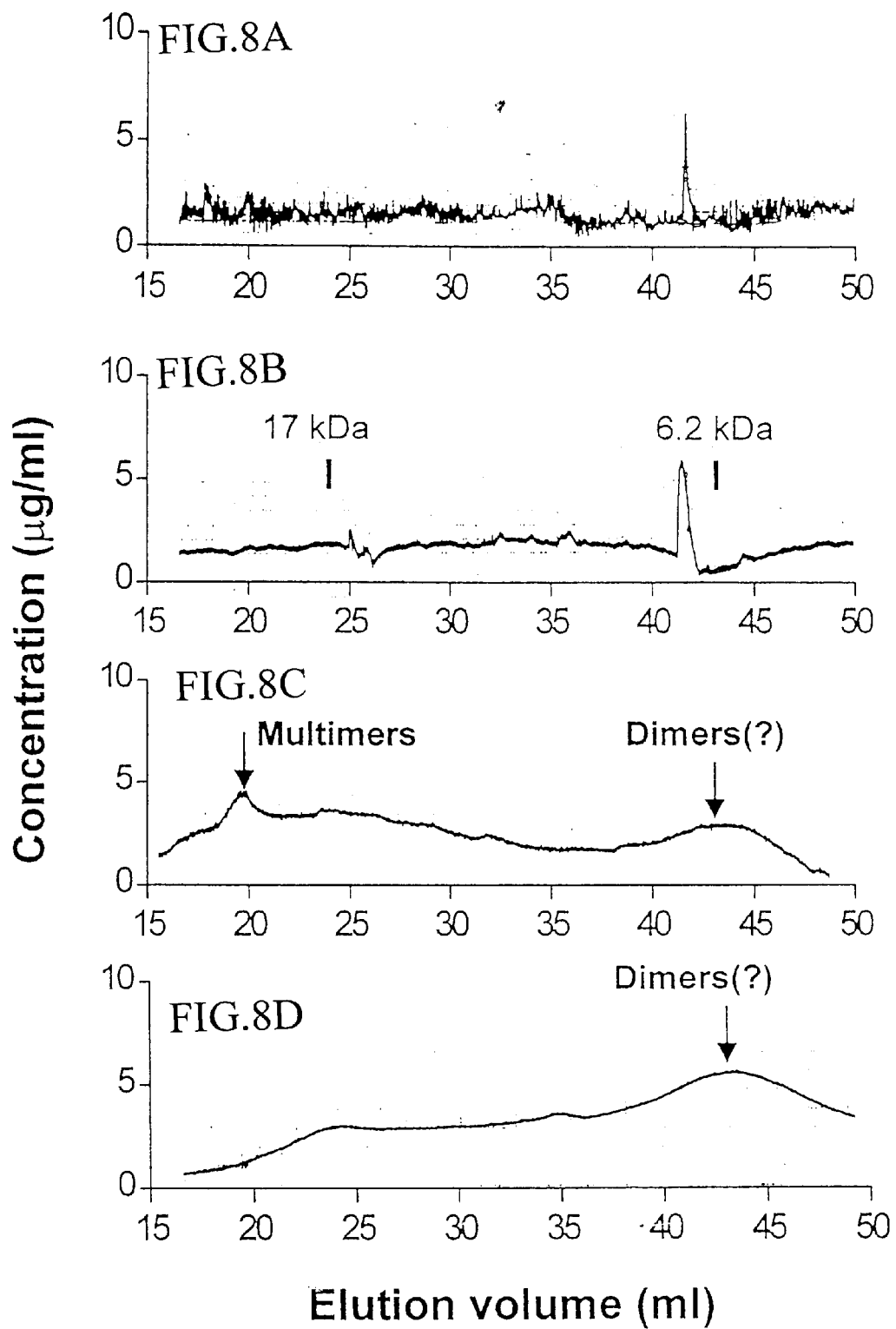

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
       (A) LENGTH: 28 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

```
Arg Met Lys Lys Lys Asp Glu Gly Ser Tyr Asp Leu Gly Lys Lys Pro
1               5                   10                  15

Ile Tyr Lys Lys Ala Pro Thr Asn Glu Phe Tyr Ala
            20                  25
```

(2) INFORMATION FOR SEQ ID NO: 2:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 2:

```
Ala Ala Arg Lys Arg Lys Gly Ser Phe Phe Tyr Gly Gly
1               5                   10
```

(2) INFORMATION FOR SEQ ID NO: 3:

(i) SEQUENCE CHARACTERISTICS:
       (A) LENGTH: 42 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 3:

```
GGCCGCTGGG CATCGAACGT CGACTTCCAC TCAGGATACA TG                    42
```

(2) INFORMATION FOR SEQ ID NO: 4:

(i) SEQUENCE CHARACTERISTICS:
       (A) LENGTH: 42 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 4:

```
GATCCATGTA TCCTGAGTGG AAGTCGACGT TCGATGCCCA GC                    42
```

(2) INFORMATION FOR SEQ ID NO: 5:

(i) SEQUENCE CHARACTERISTICS:
             (A) LENGTH: 671 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO: 5:

Met Ala Asp Val Phe Pro Ala Ala Glu Pro Ala Ala Pro Gln Asp Val
1               5                   10                  15

Ala Asn Arg Phe Ala Arg Lys Gly Ala Leu Arg Gln Lys Asn Val His
            20                  25                  30

Glu Val Lys Asn His Arg Phe Ile Ala Arg Phe Phe Lys Gln Pro Thr
        35                  40                  45

Phe Cys Ser His Cys Thr Asp Phe Ile Trp Gly Phe Gly Lys Gln Gly
50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly His Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val
    130                 135                 140

Ile Asn Val Pro Ser Leu Cys Gly Met Asp His Thr Glu Lys Arg Gly
145                 150                 155                 160

Arg Ile Tyr Leu Lys Ala Glu Val Thr Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Arg Trp Asp
    210                 215                 220

Glu Ser Phe Thr Phe Lys Leu Lys Pro Ser Asp Lys Asp Arg Arg Leu
225                 230                 235                 240

Ser Glu Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Asn Gln Glu Glu Gly Glu Tyr Tyr Asn Val Pro
        275                 280                 285

Ile Pro Glu Gly Asp Glu Glu Gly Asn Val Glu Leu Arg Gln Lys Phe
    290                 295                 300

Glu Lys Ala Lys Leu Gly Pro Ala Gly Asn Lys Val Ile Ser Pro Ser
305                 310                 315                 320

Glu Asp Arg Arg Gln Pro Ser Asn Asn Leu Asp Arg Val Lys Leu Thr
                325                 330                 335

Asp Phe Asn Phe Leu Met Val Leu Gly Lys Gly Ser Phe Gly Lys Val
            340                 345                 350

Met Leu Ala Asp Arg Lys Gly Thr Glu Glu Leu Tyr Ala Ile Lys Ile
        355                 360                 365

```
Leu Lys Lys Asp Val Val Ile Gln Asp Asp Val Glu Cys Thr Met
    370                 375                 380

Val Glu Lys Arg Val Leu Ala Leu Leu Asp Lys Pro Pro Phe Ile Thr
385                 390                 395                 400

Gln Leu His Ser Cys Phe Gln Thr Val Asp Arg Leu Tyr Phe Val Met
                405                 410                 415

Glu Tyr Val Asn Gly Gly Asp Leu Met Tyr His Ile Gln Gln Val Gly
                420                 425                 430

Lys Phe Lys Glu Pro Gln Ala Val Phe Tyr Ala Ala Glu Ile Ser Ile
            435                 440                 445

Gly Leu Phe Phe Leu His Lys Arg Gly Ile Ile Tyr Arg Asp Leu Lys
    450                 455                 460

Leu Asp Asn Val Met Leu Asp Ser Glu Gly His Ile Lys Ile Ala Asp
465                 470                 475                 480

Phe Gly Met Cys Lys Glu His Met Met Asp Gly Val Thr Thr Arg Thr
                485                 490                 495

Phe Cys Gly Thr Pro Asp Tyr Ile Ala Pro Glu Ile Ile Ala Tyr Gln
                500                 505                 510

Pro Tyr Gly Lys Ser Val Asp Trp Trp Ala Tyr Gly Val Leu Leu Tyr
            515                 520                 525

Glu Met Leu Ala Gly Gln Pro Pro Phe Asp Gly Glu Asp Glu Asp Glu
530                 535                 540

Leu Phe Gln Ser Ile Met Glu His Asn Val Ser Tyr Pro Lys Ser Leu
545                 550                 555                 560

Ser Lys Glu Ala Val Ser Ile Cys Lys Gly Leu Met Thr Lys His Pro
                565                 570                 575

Gly Lys Leu Arg Gly Cys Gly Pro Glu Gly Glu Arg Asp Val Arg Glu
            580                 585                 590

His Ala Phe Phe Arg Arg Leu Asp Trp Glu Lys Leu Glu Asn Arg Glu
            595                 600                 605

Ile Gln Pro Pro Phe Lys Pro Lys Val Cys Gly Lys Gly Ala Glu Asn
    610                 615                 620

Phe Asp Lys Phe Phe Thr Arg Gly Gln Pro Val Leu Thr Pro Pro Asp
625                 630                 635                 640

Gln Leu Val Ile Ala Asn Ile Asp Gln Ser Asp Phe Glu Gly Phe Ser
                645                 650                 655

Tyr Val Asn Pro Gln Phe Val His Pro Ile Leu Gln Ser Ala Val
            660                 665                 670
```

(2) INFORMATION FOR SEQ ID NO: 6:

(i) SEQUENCE CHARACTERISTICS:
        (A) LENGTH: 2324 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 6:

```
CCCTCTCGGC CGCCGCCCGC GCCCCCCGCG GCAGGAGGCG GCGAGGGACC ATGGCTGACG      60

TCTTCCCGGC CGCCGAGCCG GCGGCGCCGC AGGACGTGGC CAACCGCTTC GCCCGCAAAG     120

GGGCGCTGAG GCAGAAGAAC GTGCACGAGG TGAAGAACCA CCGCTTCATC GCGCGCTTCT     180

TCAAGCAGCC CACCTTCTGC AGCCACTGCA CCGACTTCAT CTGGGGGTTT GGGAAACAAG     240

GCTTCCAGTG CCAAGTTTGC TGTTTTGTGG TTCACAAGAG GTGCCATGAA TTTGTTACTT     300
```

-continued

```
TTTCTTGTCC GGGGGCGGAT AAAGGACCCG ACACAGATGA CCCGAGGAGC AAGCACAAGT      360
TCAAGATCCA CACGTATGGC AGCCCCACCT TCTGTGATCA CTGCGGCTCC CTGCTCTACG      420
GACTCATCCA CCAGGGGATG AAATGTGACA CCTGTGATAT GAACGTGCAC AAGCAGTGCG      480
TGATCAACGT GCCCAGCCTC TGCGGGATGG ACCACACGGA GAAGAGGGGC CGCATCTACC      540
TGAAGGCCGA GGTCACGGAT GAAAAGCTGC ACGTCACAGT ACGAGACGCG AAAAACCTAA      600
TCCCTATGGA TCCAAATGGG CTTTCAGATC CTTACGTGAA GCTGAAGCTT ATTCCTGACC      660
CCAAGAACGA GAGCAAACAG AAAACCAAGA CCATCCGCTC GACGCTGAAC CCCCGGTGGG      720
ACGAGTCCTT CACGTTCAAA TTAAAACCTT CTGATAAAGA CCGGCGACTG TCCGAGGAAA      780
TCTGGGACTG GGATCGAACC ACACGGAACG ACTTCATGGG GTCCCTTTCC TTTGGGGTCT      840
CGGAGCTGAT GAAGATGCCG GCCAGCGGAT GGTACAAGCT GCTGAACCAA GAGGAGGGCG      900
AGTACTACAA CGTGCCGATC CCCGAAGGCG ACGAGGAAGG CAATGTGGAG CTCAGGCAGA      960
AATTCGAGAA AGCCAAGCTT GGCCCTGCCG GCAACAAAGT CATCAGTCCC TCCGAGGACA     1020
GGAGACAGCC TTCCAACAAC CTGGACAGAG TGAAGCTCAC GGACTTCAAC TTCCTCATGG     1080
TGCTGGGCAA AGGCAGCTTT GGGAAGGTGA TGCTGGCCGA CCGGAAGGGG ACAGAGGAGC     1140
TGTACGCCAT CAAGATCCTG AAGAAGGACG TGGTCATCCA GGACGACGAC GTGGAGTGCA     1200
CCATGGTGGA GAAGCGGGTC CTGGCGCTGC TCGACAAGCC GCCGTTCCTG ACGCAGCTGC     1260
ACTCCTGCTT CCAGACGGTG GACCGGCTGT ACTTCGTCAT GGAGTACGTC AACGGCGGGG     1320
ACCTCATGTA CCACATCCAG CAGGTCGGGA AGTTCAAGGA GCCGCAAGCA GTGTTCTATG     1380
CAGCAGAGAT TTCCATCGGG CTGTTCTTTC TTCATAAAAG AGGAATCATT TATCGGGACC     1440
TGAAGTTAGA CAACGTCATG CTGGACTCGG AAGGACACAT TAAGATCGCG GACTTCGGGA     1500
TGTGCAAGGA GCACATGATG GACGGCGTCA CGACCAGGAC CTTCTGCGGG ACCCCCGACT     1560
ACATCGCCCC AGAGATAATC GCCTATCAGC CGTACGGGAA GTCCGTGGAC TGGTGGGCCT     1620
ACGGCGTCCT GTTGTACGAG ATGTTGGCCG GGCAGCCTCC GTTCGACGGC GAGGACGAGG     1680
ACGAGCTGTT CCAGTCCATC ATGGAGCACA ACGTCTCGTA CCCCAAGTCC TTGTCCAAGG     1740
AGGCCGTGTC CATCTGCAAA GGGCTGATGA CCAAGCACCC CGGGAAGCGG CTGGGCTGCG     1800
GGCCCGAGGG CGAGCGCGAC GTGCGGGAGC ATGCCTTCTT CCGGAGGATC GACTGGGAGA     1860
AGCTGGAGAA CCGTGAGATC CAGCCACCCT TCAAGCCCAA AGTGTGCGGC AAAGGAGCAG     1920
AGAACTTTGA CAAGTTCTTC ACGCGAGGGC AGCCTGTCTT GACGCCGCCC GACCAGCTGG     1980
TCATCGCTAA CATCGACCAG TCTGATTTTG AAGGCTTCTC CTACGTCAAC CCCCAGTTCG     2040
TGCACCCCAT CCTGCAGAGC GCGGTATGAG ACGCCTCGCG GAAGCCTGGT CCGCGCCCCC     2100
GCCCCCGCCT CCGCCCCCGC CGTGGGAAGC GACCCCCACC CTAGGGTTTG CCGGCCTCGG     2160
CCCTCCCTGT TCCAGGTGGA GGCCTGAAAA CTGTAGGGTG GTTGTCCCCG CGTGCTCGGC     2220
TGCGTCATCT CAGCGGAAGA TGACGTCACG TCGGCATCTG CTTGACGTAG AGGTGACATC     2280
TGGCGGGGA TTGACCCTTT CTGGAAAGCA AACAGACTCT GGCC                      2324
```

(2) INFORMATION FOR SEQ ID NO: 7:

(i) SEQUENCE CHARACTERISTICS:
        (A) LENGTH: 792 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 7:

```
ACGGACTTCA ACTTCCTCAT GGTGCTGGGC AAAGGCAGCT TTGGGAAGGT GATGCTGGCC      60
GACCGGAAGG GGACAGAGGA GCTGTACGCC ATCAAGATCC TGAAGAAGGA CGTGGTCATC     120
CAGGACGACG ACGTGGAGTG CACCATGGTG GAGAAGCGGG TCCTGGCGCT GCTCGACAAG     180
CCGCCGTTCC TGACGCAGCT GCACTCCTGC TTCCAGACGG TGGACCGGCT GTACTTCGTC     240
ATGGAGTACG TCAACGGCGG GGACCTCATG TACCACATCC AGCAGGTCGG GAAGTTCAAG     300
GAGCCGCAAG CAGTGTTCTA TGCAGCAGAG ATTTCCATCG GGCTGTTCTT TCTTCATAAA     360
AGAGGAATCA TTTATCGGGA CCTGAAGTTA GACAACGTCA TGCTGGACTC GGAAGGACAC     420
ATTAAGATCG CGGACTTCGG GATGTGCAAG GAGCACATGA TGGACGGCGT CACGACCAGG     480
ACCTTCTGCG GGACCCCCGA CTACATCGCC CCAGAGATAA TCGCCTATCA GCCGTACGGG     540
AAGTCCGTGG ACTGGTGGGC CTACGGCGTC CTGTTGTACG AGATGTTGGC CGGGCAGCCT     600
CCGTTCGACG GCGAGGACGA GGACGAGCTG TTCCAGTCCA TCATGGAGCA CAACGTCTCG     660
TACCCCAAGT CCTTGTCCAA GGAGGCCGTG TCCATCTGCA AAGGGCTGAT GACCAAGCAC     720
CCCGGGAAGC GGCTGGGCTG CGGGCCCGAG GGCGAGCGCG ACGTGCGGGA GCATGCCTTC     780
TTCCGGAGGA TC                                                        792
```

(2) INFORMATION FOR SEQ ID NO: 8:

(i) SEQUENCE CHARACTERISTICS:
        (A) LENGTH: 330 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Met Ser Asp Ser Glu Lys Leu Asn Leu Asp Ser Ile Ile Gly Arg Leu
 1               5                  10                  15

Leu Glu Val Gln Gly Ser Arg Pro Gly Lys Asn Val Gln Leu Thr Glu
            20                  25                  30

Asn Glu Ile Arg Gly Leu Cys Leu Lys Ser Arg Glu Ile Phe Leu Ser
        35                  40                  45

Gln Pro Ile Leu Leu Glu Leu Glu Ala Pro Leu Lys Ile Cys Gly Asp
    50                  55                  60

Ile His Gly Gln Tyr Tyr Asp Leu Leu Arg Leu Phe Glu Tyr Gly Gly
65                  70                  75                  80

Phe Pro Pro Glu Ser Asn Tyr Leu Phe Leu Gly Asp Tyr Val Asp Arg
                85                  90                  95

Glu Lys Gln Ser Leu Glu Thr Ile Cys Leu Leu Leu Ala Tyr Lys Ile
            100                 105                 110

Lys Tyr Pro Glu Asn Phe Phe Leu Leu Arg Gly Asn His Glu Cys Ala
        115                 120                 125

Ser Ile Asn Arg Ile Tyr Gly Phe Tyr Asp Glu Cys Lys Arg Arg Tyr
    130                 135                 140

Asn Ile Lys Leu Trp Lys Thr Phe Thr Asp Cys Phe Asn Cys Leu Pro
145                 150                 155                 160

Ile Ala Ala Ile Val Asp Glu Lys Ile Phe Cys Cys His Gly Gly Leu
                165                 170                 175

Ser Pro Asp Leu Gln Ser Met Glu Gln Ile Arg Arg Ile Met Arg Pro
            180                 185                 190
```

Thr Asp Val Pro Asp Gln Gly Leu Leu Cys Asp Leu Leu Trp Ser Asp
            195                 200                 205

Pro Asp Lys Asp Val Gln Gly Trp Gly Glu Asn Asp Arg Gly Val Ser
    210                 215                 220

Phe Thr Phe Gly Ala Glu Val Val Ala Lys Phe Leu His Lys His Asp
225                 230                 235                 240

Leu Asp Leu Ile Cys Arg Ala His Gln Val Val Glu Asp Gly Tyr Glu
                245                 250                 255

Phe Phe Ala Lys Arg Gln Leu Val Thr Leu Phe Ser Ala Pro Asn Tyr
                260                 265                 270

Cys Gly Glu Phe Asp Asn Ala Gly Ala Met Met Ser Val Asp Glu Thr
            275                 280                 285

Leu Met Cys Ser Phe Gln Ile Leu Lys Pro Ala Asp Lys Asn Lys Gly
    290                 295                 300

Lys Tyr Gly Gln Phe Ser Gly Leu Asn Pro Gly Gly Arg Pro Ile Thr
305                 310                 315                 320

Pro Pro Arg Asn Ser Ala Lys Ala Lys Lys
                325                 330

(2) INFORMATION FOR SEQ ID NO: 9:

(i) SEQUENCE CHARACTERISTICS:
       (A) LENGTH: 1367 base pairs
       (B) TYPE: nucleic acid
       (C) STRANDEDNESS: single
       (D) TOPOLOGY: linear (ii) MOLECULE TYPE: peptide (xi) SEQUENCE DESCRIPTION: SEQ ID NO: 9:

```
GGGCAAGGAG CTGCTGGCTG ACGGCGGCA TGTCCGACAG CGAGAAGCTC AACCTGGACT      60
CGATCATCGG GCGCCTGCTG GAAGTGCAGG GCTCGCGGCC TGGCAAGAAT GTACAGCTGA    120
CAGAGAACGA GATCCGCGGT CTGTGCCTGA AATCCCGGGA GATTTTTCTG AGCCAGCCCA    180
TTCTTCTGGA GCTGGAGGCA CCCCTCAAGA TCTGCGGTGA CATACACGGC CAGTACTACG    240
ACCTTCTGCG ACTATTTGAG TATGGCGGTT TCCCTCCCGA GAGCAACTAC CTCTTTCTGG    300
GGACTATGT GGACAGGGGC AAGCAGTCCT TGGAGACCAT CTGCCTGCTG CTGGCCTATA     360
AGATCAAGTA CCCCGAGAAC TTCTTCCTGC TCCGTGGGAA CCACGAGTGT GCCAGCATCA    420
ACCGCATCTA TGGTTTCTAC GATGAGTGCA AGAGACGCTA CAACATCAAA CTGTGGAAAA    480
CCTTCACTGA CTGCTTCAAC TGCCTGCCCA TCGCGGCCAT AGTGGACGAA AAGATCTTCT    540
GCTGCCACGG AGGCCTGTCC CCGGACCTGC AGTCTATGGA GCAGATTCGG CGGATCATGC    600
GGCCCACAGA TGTGCCTGAC CAGGGCCTGC TGTGTGACCT GCTGTGGTCT GACCCTGACA    660
AGGACGTGCA GGGCTGGGGC GAGAACGACC GTGGCGTCTC TTTTACCTTT GGAGCCGAGG    720
TGGTGGCCAA GTTCCTCCAC AAGCACGACT TGGACCTCAT CTGCCGAGCA CACCAGGTGG    780
TAGAAGACGG CTATGAGTTC TTTGCCAAGC GGCAGCTGGT GACACTTTTC TCAGCTCCCA    840
ACTACTGTGG CGAGTTTGAC AATGCTGGCG CCATGATGAG TGTGGACGAG ACCCTCATGT    900
GCTCTTTCCA GATCCTCAAG CCCGCCGACA AGAACAAGGG GAAGTACGGG CAGTTCAGTG    960
GCCTGAACCC TGGAGGCCGA CCCATCACCC CACCCCGCAA TTCCGCCAAA GCCAAGAAAT   1020
AGCCCCCGCA CACCCCCTG TGCCCCAGAT GATGGATTGA TTGTACAGAA ATCATGCTGC    1080
CATGCTGGGG GGGGGTCACC CCGACCCCTA AGGCCCACCT GTCACGGGGA ACATGGAGCC   1140
```

```
TTGGTGTATT TTTCTTTTCT TTTTTTAATG AATCAATAGC AGCGTCCAGT CCCCCAGGGC    1200

TGCTTCCTGC CTGCACCTGC GGTACTGTGA GCAGGATCCT GGGGCCGAGG CTGCAGCTCA    1260

GGGCAACGGC AGGCCAGGTC GTGGGTCTCC AGCCGTGCTT GGCCTCAGGC TGGCAGCCCG    1320

GATCCTGGGG CAACCCATCT GGTCTCTTGA ATAAAGGTCA AAGCTGG                  1367

(2) INFORMATION FOR SEQ ID NO: 10:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Met Asp Glu Lys Val Phe Thr Lys Glu Leu Asp Gln Trp Ile Glu Gln
1               5                   10                  15

Leu Asn Glu Cys Lys Gln Leu Ser Glu Ser Gln Val Lys Ser Leu Cys
            20                  25                  30

Arg Arg Leu Lys Lys Ser Trp Thr Lys Glu Ser Asn Val Gln Glu Val
        35                  40                  45

Arg Cys Pro Val Thr Val Arg Gly Asp Val His Gly Gln Phe His Asp
    50                  55                  60

Leu Met Glu Leu Phe Arg Ile Gly Gly Lys Ser Pro Asp Thr Asn Tyr
65                  70                  75                  80

Leu Phe Met Gly Asp Tyr Val Asp Arg Gly Tyr Tyr Ser Val Glu Thr
                85                  90                  95

Val Thr Leu Leu Val Ala Leu Lys Val Arg Tyr Arg Glu Arg Ile Thr
            100                 105                 110

Ile Leu Arg Gly Asn His Glu Ser Arg Gln Ile Thr Gln Val Tyr Gly
        115                 120                 125

Phe Tyr Asp Glu Cys Leu Arg Lys Tyr Gly Asn Ala Asn Val Trp Lys
130                 135                 140

Tyr Phe Thr Asp Leu Phe Asp Tyr Leu Pro Ile Thr Ala Leu Val Asp
145                 150                 155                 160

Gly Gln Ile Phe Cys Leu His Gly Gly Leu Ser Pro Ser Ile Asp Thr
                165                 170                 175

Leu Asp His Ile Arg Ala Leu Asp Arg Leu Gln Glu Val Pro His Glu
            180                 185                 190

Gly Pro Met Cys Asp Leu Leu Trp Ser Asp Pro Asp Asp Arg Gly Gly
        195                 200                 205

Trp Gly Ile Ser Pro Arg Gly Ala Gly Tyr Thr Phe Gly Gln Asp Ile
    210                 215                 220

Ser Glu Thr Phe Asn His Ala Asn Gly Leu Thr Leu Val Ser Arg Ala
225                 230                 235                 240

His Gln Leu Val Met Glu Gly Tyr Asn Trp Cys His Asp Arg Asn Val
                245                 250                 255

Val Thr Ile Phe Ser Ala Pro Asn Tyr Cys Tyr Arg Cys Gly Asn Gln
            260                 265                 270

Ala Ala Ile Met Glu Leu Asp Asp Thr Leu Lys Tyr Ser Phe Leu Gln
        275                 280                 285

Phe Asp Pro Ala Pro Ala Glu Ala Ser His Met Leu Leu Val Val Pro
    290                 295                 300

Gln Thr Thr Ser Cys Asn Glu Ile Leu Asn Leu Tyr Ser Ile Ala Met
```

Asn His Ile Leu Thr
              325

(2) INFORMATION FOR SEQ ID NO: 11:

(i) SEQUENCE CHARACTERISTICS:
        (A) LENGTH: 1721 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 11:

| | | | | | |
|---|---|---|---|---|---|
| TCACAAATAC | CCCGGGAACC | GCGGCGGCGT | GTGCGTGTGG | CCGCGTGTGC | GGCGGCGGCG | 60 |
| CGGGAGGAGC | CGGGAGCGGC | AGCCGGTTCG | GGCGGGTGGC | ATCATGGACG | AGAAGGTGTT | 120 |
| CACCAAGGAG | CTGGACCAGT | GGATCGAGCA | GCTGAACGAG | TGCAAGCAGC | TGTCTGAGTC | 180 |
| CCAGGTTAAG | AGCCTCTGCA | GAAGGCTAAA | GAAATCCTGG | ACAAAAGAAT | CCAATGTGCA | 240 |
| AGAAGTTCGA | TGTCCAGTCA | CTGTCCGTGG | AGATGTGCAT | GGGCAATTTC | ATGATCTCAT | 300 |
| GGAACTGTTT | AGAATTGGTG | GCAAATCACC | AGATACAAAT | TACTTGTTTA | TGGGCGATTA | 360 |
| TGTTGACAGA | GGATATTATT | CAGTGGAAAC | AGTTACTCTG | CTTGTAGCTC | TTAAGGTTCG | 420 |
| TTACCGTGAA | CGTATCACCA | TTCTTCGAGG | AAATCATGAG | AGCAGACAGA | TCACACAAGT | 480 |
| ATATGGTTTC | TACGATGAGT | GTTTAAGGAA | ATACGGAAAT | GCAAATGTTT | GGAAGTATTT | 540 |
| TACAGACCTT | TTTGACTATC | TTCCTCTCAC | TGCCTTGGTG | GATGGGCAGA | TCTTCTGTCT | 600 |
| ACATGGTGGC | CTCTCACCAT | CCATAGATAC | ACTGGATCAC | ATCAGAGCAC | TTGATCGCCT | 660 |
| ACAAGAAGTT | CCTCATGAGG | GTCCAATGTG | TGACTTGCTG | TGGTCAGATC | CAGATGACCG | 720 |
| TGGAGGTTGG | GGTATATCTC | CTCGAGGAGC | TGGTTACACC | TTTGGGCAGG | ATATTTCTGA | 780 |
| GACATTTAAT | CATGCCAATG | GCCTCACGTT | GGTGTCTAGA | GCTCATCAGC | TGGTGATGGA | 840 |
| GGGATATAAC | TGGTGCCATG | ACCGAAATGT | AGTAACGATT | TCAGTGCTC | CAAACTATTG | 900 |
| TTATCGTTGT | GGTAACCAAG | CTGCAATCAT | GGAACTTGAT | GATACTCTAA | AATACTCTTT | 960 |
| CTTGCAGTTT | GACCCAGCAC | CCGCAGAGGC | GAGCCACATG | TTACTCGTCG | TACCCCAGAC | 1020 |
| TACTTCCTGT | AATGAAATTT | TAAACTTGTA | CAGTATTGCC | ATGAACCATA | TATTGACCTA | 1080 |
| ATGGATATGG | GAAGAGCAAC | AGTAACTCCA | CAAGTGTCAG | AGAATAGTTA | ACATTCAAAA | 1140 |
| AAACTTGTTT | TCACACGGAC | CAAAAAGATG | TGCCATATAA | AAATACAAAG | CCTGTCATCA | 1200 |
| ACAGCCGTGA | CCACTTTAGA | ATGAACCAGT | TCATTGCATG | CTGAAGCGAC | ATTGTTGGTC | 1260 |
| AAGAAACCAG | TTTCTGGCAT | AGCGCTATTT | GTAGTTACTT | TGCTTTCTCT | GAGAGACTGC | 1320 |
| AGATAAGATG | TAAACATTAA | CACCTCGTGA | ATACAATTTA | ACTTCCATTT | AGCTATAGCT | 1380 |
| TTACTCAGCA | TGACTGTAGG | ATAAGAATAG | CAGCAAACAA | TCATTGGAGC | TTAATGAACA | 1440 |
| TTTTTAAAAA | TAAGTACCAA | GGCCTCCCCT | CTACTTGTGA | GTTTTAAAAT | CGTTTTTGTT | 1500 |
| TATTTTCAGG | GTACCGTTTA | ATTTAATTGT | ATGATTTGTC | TCGCATCAGT | TTATTTTCCC | 1560 |
| TCTCAAATCT | AGCCTCATGT | TGTTCTTTGT | TACTGTCACA | ACCTGGTGAG | TTGTTTTGAA | 1620 |
| TGGAATTGTT | TTTTTTCTC | CCTGCTGTAA | GATGATGTTA | CTGCACAAGA | GCACTGCAGT | 1680 |
| GTTTTTCATA | ATAAACTTGT | GAACTAAGAG | ATGAAAAAGT | C | | 1721 |

(2) INFORMATION FOR SEQ ID NO: 12:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO: 12:

TGTTACCAAT CTGAAGTGGG AGCGGCCGCA TCTTTTTTTT TTTTTTTTTT                   50

(2) INFORMATION FOR SEQ ID NO: 13:

(i) SEQUENCE CHARACTERISTICS:
            (A) LENGTH: 481 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO: 13:

TTGACCTAAC ACCAAATTTA TCACTTTTTA AAAACAAGAG ATTTTCCCCA AAAGTGAAGG        60

AATAAGAAAC AAATCCGGTG TCCATGCATT CCCAAACTGC AGTCTTGATC CCAAGATACC      120

TCCTCCTCTC TCAGACCGAG TTGGCTCCCT TGGAATCCAG TGGTGGTATA TGGGTTGAGG      180

GTTCTTTTGT GCTGGGTTCC TTACTGCCTC TCTCGTGAGT TTAGGGATG CATTCTGCAG       240

TTTTTTTTGC TGTCCCAGAG GTGCCCAGCC TTGACTCCAC TTCTGTGTCT GGGATCCCAG      300

GTGGGCGGGA CTCCTGGGTT CCTGTGCTCT CAGCGGCCCC CTCAGGTTCC TCTCCTTGCT      360

GCTGTTGCCC CAGGTGATGT TCAACCATCA TCTGGAGCTC TTTCATTGTG GGTGTGATCC      420

TTGTCATCTT CTTCCGTTGC CGTGGAGACA TTGCCAAAGT GGACTTGAGA TGTGGGTTGG      480

G                                                                     481

(2) INFORMATION FOR SEQ ID NO: 14:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO: 14:

GAATTCGGCA CGAG                                                         14

(2) INFORMATION FOR SEQ ID NO: 15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO: 15:

CTCGAGTTTT TTTTTTTTTT TTTT                                              24

(2) INFORMATION FOR SEQ ID NO: 16:

(i) SEQUENCE CHARACTERISTICS:
            (A) LENGTH: 439 base pairs
            (B) TYPE: nucleic acid

```
            (C) STRANDEDNESS: single
            (D) TOPOLOGY: linear (ii) MOLECULE TYPE: peptide (xi) SEQUENCE DESCRIPTION: SEQ ID NO: 16:

GACTTCCTCT ATGGTGGCGT CGGCGAACAG CCCCGCGGGA ATGTCGACGA GGAGCTGAGC      60

AAAAAATCCC AGAAGTGGGA TGAAATGAAC ATCTTGGCGA CGTATCATCC AGCAGACAAA     120

GACTATGGTT TAATGAAAAT AGATGAACCA AGCACTCCTT ACCATAGTAT GATGGGGGAT     180

GATGAAGATG CCTGTAGTGA CACCGAGGCC ACTTGAAGCC ATGGCGCCAG ACATCTTTAG     240

CCAGGAAATT AGCTGCAGCT GAAGGCTTGG AGCCAAAGTA TCGGATTCAG GAACAAGAAA     300

GCAGTGGAGA GGAGGATAGT GACCTCTCAC CTGAAGAACG AGAAAAAAAG CGACAATTTG     360

AAATGAAAAG GAAGCTTCAC TACAATGAAG GACTCAATAT CAAACTAGCC AGACANTTAA     420

TTTCAAAAGA CCTACATGA                                                  439

(2) INFORMATION FOR SEQ ID NO: 17:

(i) SEQUENCE CHARACTERISTICS:
        (A) LENGTH: 250 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Phe Glu Glu Leu Glu Phe Leu Ser
        35                  40                  45

Thr Ile Asn Val Gly Leu Thr Ser Ile Ala Asn Leu Pro Lys Leu Asn
    50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Thr His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Asp Glu Asp Glu
                165                 170                 175

Glu Glu Tyr Asp Glu Asp Ala Gln Val Glu Asp Glu Glu Asp Glu
            180                 185                 190

Asp Glu Glu Glu Glu Gly Glu Glu Asp Val Ser Gly Glu Glu
        195                 200                 205

Glu Asp Glu Glu Gly Tyr Asn Asp Gly Glu Val Asp Asp Glu Asp
    210                 215                 220

Glu Glu Glu Leu Gly Glu Glu Glu Arg Gly Gln Lys Arg Lys Arg Arg
```

```
225                 230                 235                 240
Glu Pro Glu Asp Glu Gly Glu Asp Asp Asp
                245                 250
```

(2) INFORMATION FOR SEQ ID NO: 18:

(i) SEQUENCE CHARACTERISTICS:
        (A) LENGTH: 750 base pairs
        (B) TYPE: nucleic acid
        (C) STRANDEDNESS: single
        (D) TOPOLOGY: linear (ii) MOLECULE TYPE: nucleotide sequence (xi) SEQUENCE DESCRIPTION: SEQ ID NO: 18:

```
ATGGAGATGG GCAGACGGAT TCATTTAGAG CTGCGGAACA GGACGCCCTC TGATGTGAAA      60

GAACTTGTCC TGGACAACAG TCGGTCGAAT GAAGGCAAAC TCGAAGGCCT CACAGATGAA     120

TTTGAAGAAC TGGAATTCTT AAGTACAATC AACGTAGGCC TCACCTCAAT CGCAAACTTA     180

CCAAAGTTAA CAAACTTAA GAAGCTTGAA CTAAGCGATA ACAGAGTCTC AGGGGGCCTG     240

GAAGTATTGG CAGAAAAGTG TCCGAACCTC ACGCATCTAA ATTTAAGTGG CAACAAAATT     300

AAAGACCTCA GCACAATAGA GCCACTGAAA AAGTTAGAAA ACCTCAAGAG CTTAGACCTT     360

TTCAATTGCG AGGTAACCAA CCTGAACGAC TACCGAGAAA ATGTGTTCAA GCTCCTCCCG     420

CAACTCACAT ATCTCGACGG CTATGACCGG GACGACAAGG AGGCCCCTGA CTCGGATGCT     480

GAGGGCTACG TGGAGGGCCT GGATGATGAG GAGGAGGATG AGGATGAGGA GGAGTATGAT     540

GAAGATGCTC AGGTAGTGGA AGACGAGGAG GACGAGGATG AGGAGGAGGA AGGTGAAGAG     600

GAGGACGTGA GTGGAGAGGA GGAGGAGGAT GAAGAAGGTT ATAACGATGG AGAGGTAGAT     660

GACGAGGAAG ATGAAGAAGA GCTTGGTGAA GAAGAAAGGG GTCAGAAGCG AAAACGAGAA     720

CCTGAAGATG AGGGAGAAGA TGATGACTAA                                     750
```

(2) INFORMATION FOR SEQ ID NO: 19:

(i) SEQUENCE CHARACTERISTICS:
        (A) LENGTH: 202 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

```
Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
                20                  25                  30

Pro Thr Pro Ala Met Leu Phe Arg Leu Ser Glu His Ser Ser Pro Glu
            35                  40                  45

Glu Glu Ala Ser Pro His Gln Arg Ala Ser Gly Glu Gly His His Leu
        50                  55                  60

Lys Ser Lys Arg Ser Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Gly Glu Asn Gln Ala Ser Glu Glu Asp Glu Leu Gly Glu Leu Arg
            100                 105                 110

Glu Leu Gly Tyr Pro Arg Glu Glu Glu Glu Glu Glu Glu Glu Asp
```

```
            115                 120                 125
Glu Glu Glu Glu Glu Asp Ser Gln Ala Glu Val Leu Lys Gly Ser Arg
    130                 135                 140

Gly Ser Ala Gly Gln Lys Thr Thr Tyr Gly Gln Gly Leu Glu Gly Pro
145                 150                 155                 160

Trp Glu Arg Pro Pro Pro Leu Asp Gly Pro Gln Arg Asp Gly Ser Ser
                165                 170                 175

Glu Asp Gln Val Glu Asp Pro Ala Leu Asn Glu Pro Gly Glu Pro
            180                 185                 190

Gln Arg Pro Ala His Pro Glu Pro Gly Thr
        195                 200

(2) INFORMATION FOR SEQ ID NO: 20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Asp Ala Arg Pro Pro
1               5

(2) INFORMATION FOR SEQ ID NO: 21:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Asp Ala Arg Pro Pro
1               5

(2) INFORMATION FOR SEQ ID NO: 22:

(i) SEQUENCE CHARACTERISTICS:
        (A) LENGTH: 1691 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO: 22:

AGCGAAACAG AGACAGAGGG AGACTCGCGG AGAGGGAGCA AGGGAGATAG AGGAAGGTTG      60

GAGAGACACA GAGAGAGCGA GGGAAGGAGG GCCAGAGACC AGCCCCGCGA GCCCGAGGTG     120

CGGCCCCAGG GGACCGGGCA CCCAGGAGCC CCAGAGCCGC GAGCCGGCCG CCCCCCACCC     180

CCGCGCGCCC TCCCCTCGCC GGCGGGTATT TTTATCTGTG CGTGAACAGC CCTCCAGCTC     240

CTCTCTGCCA CACTCAACCC GCTGCCGCCG CGGCCCGGAG CAGCGCGGGG GAGCGGAGCG     300

GGATCGCAGC CCGAGACCCC ACGACGCGCG CCCCGCCCGC CATGGACCCC AAAGACCGCA     360

AGAAGATCCA GTTCTCCGTG CCCGCGCCCC CCAGCCAGCT CGACCCCCGC CAGGTGGAGA     420

TGATCCGGCG CAGGAGACCA ACCCCTGCCA TGCTGTTCCG GCTCTCAGAG CACTCCTCAC     480

CAGAGGAGGA GGCCTCACCC CACCAGAGAG CCTCAGGAGA GGGGCACCAC CTCAAGTCGA     540
```

```
AGAGATCCAA TCCTTGTGCC TACACACCCC CCTCGCTGAA AGCCGTCCAG CGCATTGCTG      600

AGTCTCACCT GCAGTCCATC AGCAACCTGG GTGAGAACCA GGCCTCGGAG GAGGAGGATG      660

AGCTGGGGGA GCTGCGGGAA CTGGGCTACC AAGAGAGGA AGAGGAGGAG GAAGAGGAGG       720

AGGATGAAGA GGAGGAGGAG GACAGCCAGG CGGAAGTCCT GAAGGGCAGC AGGGGGTCTG      780

CTGGGCAGAA GACAACTTAT GGCCAAGGTC TGGAGGGTCC CTGGGAGCGC CCGCCTCCTC     840

TGGATGGGCC CCAGAGAGAC GGAAGCTCTG AGGACCAAGT GGAAGACCCA GCATTGAATG     900

AACCCGGGGA GGAGCCACAG CGCCCTGCCC ACCCTGAGCC TGGCACATAG GCACCCAGCC    960

CTGCATCTCC TGGAAGGAAG TGGGAGGAAG CATTGATGTT CTCCAGAAAC CCATTCTGTT    1020

CACACCCTAT TTTGTACCCT GCTTCTCACT TGCTAGGGCT GCGGCTTCTG ACTTTTAGAA    1080

GACTAAGGCT GGTCTGTGTT TGCTTGTCTG CCCAACTTCG CTGATCCCAG AGTCCCTGGG    1140

CACTTGCTGC CTGATGCCTA CCCCTGCCAG TCATTCCCCC ATACACCCAG CAGGAGGTGG    1200

GATGGGAGAG CTTGCATTGG GAAATCCAGT AAATGGGGGA CAAAGATTCA TCCTTCACAA    1260

TTCTACTCCC TAGACCCTCT CCCCTGGGCG TAGGAAACCA CAGGGCAGGA CCCTAAGATC    1320

TGGGGAAAAG GGATACTGAG AACTTGTAAG TGCCCATAGA TCTTTCTCCA TCCCCTGGGC   1380

AATTCCAAGT CATCACCCCT TCACTGCCTT CTACCAGGGC CCAGAATTCA GGCATCTTTT   1440

CCACGGCCTC AGCTTTTGGT AAATCTTCCC CTTATCACCT GCTCCCCAGC CTGGGTGCCT   1500

GGAAGATGGA CTGGCAGAGA CTGCTTTGCT GCATTTTATG TGTGCTTTGA TGCCAGGAAT   1560

GCCACCTAGT ATAATAAGTC CTTAGGGGGG CACATGGTGG GGGAGCCAAG CTCTCCTTGT   1620

CCTCCAGCTG CTCTGTCCCC TTCCCCTCTT CCCTGACTCC CGGCCTGAAC CTGTAATAAA   1680

TCTTTGTAAA T                                                         1691

(2) INFORMATION FOR SEQ ID NO: 23:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Lys Lys Asp Glu Gly Ser Tyr
1               5

(2) INFORMATION FOR SEQ ID NO: 24:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Phe Lys Leu Lys Arg Lys Gly Ser Phe Lys Lys Phe Ala
1               5                   10

(2) INFORMATION FOR SEQ ID NO: 25:

(i) SEQUENCE CHARACTERISTICS:
        (A) LENGTH: 28 amino acids
        (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO: 25:

Arg Met Lys Lys Lys Asp Glu Gly Ser Tyr Asp Leu Gly Lys Lys Pro
1               5                   10                  15

Ile Tyr Lys Lys Ala Pro Thr Asn Glu Phe Tyr Ala
                20                  25
```

STIMULATION OF ANGIOGENESIS VIA SYNDECAN-4 CYTOPLASMIC DOMAIN SIGNALING PATHWAY

PROVISIONAL PATENT APPLICATION

The subject matter as a whole comprising the present invention was first filed with the U.S. Patent and Trademark Office as Provisional Patent Application No. 60/073,711 on Feb. 4, 1998.

RESEARCH SUPPORT

The research effort for the invention was supported by grants from National Institutes of Health Grant HL-53793; the National Institutes of Health Training Grant HL-07374; and American Heart Association Scientist Development Grant 9730282N.

FIELD OF THE INVENTION

The present invention is concerned generally with the stimulation of angiogenesis in living tissues and organs; and is particularly directed to the regulation of syndecan-4 cytoplasmic domain phosphorylation within endothelial cells in-situ.

BACKGROUND OF THE INVENTION

Angiogenesis, by definition, is the formation of new capillaries and blood vessels within living tissues; and is a complex process first recognized in studies of wound healing and then within investigations of experimental tumors. Angiogenesis is thus a dynamic process which involves extracellular matrix remodeling, endothelial cell migration and proliferation, and functional maturation of endothelial cells into mature blood vessels [Brier, G. and K. Alitalo, *Trends Cell Biology* 6: 454–456 (1996)]. Clearly, in normal living subjects, the process of angiogenesis is a normal host response to injury; and as such, is an integral part of the host body's homeostatic mechanisms.

It will be noted and appreciated, however, that whereas angiogenesis represents an important component part of tissue response to ischemia, or tissue wounding, or tumor-initiated neovascularization, relatively little new blood vessel formation or growth takes place in most living tissues and organs in mature adults (such as the myocardium of the living heart) [Folkman, J. and Y. Shing, *J. Biol. Chem.* 267: 10931–10934 (1992); Folkman, J., *Nat. Med.* 1: 27–31 (1995); Ware, J. A. and M. Simons, *Nature Med.* 3: 158–164 (1997)]. Moreover, although regulation of an angiogenetic response in-vivo is a critical part of normal and pathological homeostasis, little is presently known about the control mechanisms for this process.

A number of different growth factors and growth factor receptors have been found to be involved in the process of stimulation and maintenance of angiogenetic responses. In addition, a number of extracellular matrix components and cell membrane-associated proteins are thought to be involved in the control mechanisms of angiogenesis. Such proteins include SPARC [Sage et al., *J. Cell Biol.* 109: 341–356 (1989); Motamed, K. and E. H. Sage, *Kidney Int.* 51: 1383–1387 (1997)]; thrombospondin 1 and 2 respectively [Folkman, J., *Nat. Med.* 1: 27–31 (1995); Kyriakides et al., *J. Cell Biol.* 140: 419–430 (1998)]; and integrins $\alpha v \beta 5$ and $\alpha v \beta 3$ [Brooks et al., *Science* 264: 569–571 (1994); Friedlander et al., *Science* 270: 1500–1502 (1995)]. However, it is now recognized that a major role is played by heparan-binding growth factors such as basic fibrocyte growth factor (bFGF) and vascular endothelial growth factor (VEGF); and thus the regulation of angiogenesis involves the extracellular heparan sulfate matrix and the core proteins at the surface of endothelial cells.

While growth factor signalling generally occurs through specific high-affinity receptors, several growth factors are now known to interact with adjacent, membrane-anchored, proteoglycan co-receptors. In particular, bFGF requires binding to a specific sequence of sulfated polysaccharides in the extracellular heparan sulfate glycosaminoglycan (GAG) chain [Turnbull et al., *J. Biol. Chem.* 267: 10337–10341 (1992)] in order to bind to its high-affinity receptor on the cell surface and to exert its effect on the target cells [Olwin, B. B., and A. Rapraeger, *J. Cell Biol.* 118: 631–639 (1992); Rapraeger et al., *Science* 252: 1705–1708 (1991)]. The current picture of the role of heparan sulfate in the binding mechanism of bFGF involves dimerization of the growth factor as well as direct heparan sulfate binding to the high-affinity receptor [Brickman et al., *J. Biol. Chem.* 270: 24941–24948 (1995); Kan et al., *Science* 259: 1918–1921 (1993)]. Together, these events lead to receptor multimerization and to tyrosine trans-phosphorylation of adjacent FGF receptor cytoplasmic tails, followed by phosphorylation of other downstream substrates [Krufka et al., *Biochemistry* 35: 11131–11141 (1996); van der Geer et al., *Annu. Rev. Cell Biol.* 10: 251–337 (1994)].

Research investigations have shown that heparan sulfate core proteins or proteoglycans mediate both heparin-binding growth factors and receptor interaction at the cell surface; and that accumulation and storage of such growth factors within the extracellular matrix proper typically occurs [Vlodavsky et al., *Clin. Exp. Metastasis* 10: 65 (1992); Olwin, B. B. and A. Rapraeger, *J. Cell Biol.* 118: 631–639 (1992); Rapraeger, A. C., *Curr. Opin. Cell Biol.* 5: 844–853 (1993)]. The presence of heparin or heparan sulfate is thus required for bFGF-dependent activation of cell growth in-vitro [Yayon et al., *Cell* 64: 841–848 (1991); Rapraeger et al., *Science* 252: 1705–1708 (1991)]; and the removal of heparan sulfate chains from the cell surface and extracellular matrix by enzymatic digestion greatly impairs bFGF activity and inhibits neovascularization in-vivo [Sasisekharan et al., *Proc. Natl. Acad. Sci. USA* 91: 1524–1528 (1994)]. Ample scientific evidence now exists which demonstrates that any meaningful alteration of heparan sulfate (HS) chain composition on the cell surface or within the extracellular matrix (which can be initiated by means of an altered synthesis, or a degradation, or a substantive modification of glycosaminoglycan chains) can meaningfully affect the intracellular signaling cascade initiated by the growth factor. The importance of heparan sulfate in growth factor-dependent signaling has become well recognized in this field.

Heparan sulfate (HS) chains on the cell surface and within the extracellular matrix are present via a binding to a specific category of proteins commonly referred to as "proteoglycans". This category is constituted of several classes of core proteins, each of which serve as acceptors for a different type of glycosaminoglycan (GAG) chains. The GAGs are linear co-polymers of N-acetyl-D-glycosamine [binding heparan sulfate] or N-acetyl-D-galactosamine [binding chondroitin sulfate (CS) chains] and aoidic sugars which are attached to these core proteins via a linking tetrasaccharide moiety. Three major classes of HS-carrying core proteins are present in living endothelial cells: cell membrane-spanning syndecans, GPI-linked glypicans, and a secreted perlecan core protein [Rosenberg et al., *J. Clin. Invest.* 99: 2062–2070 (1997)]. While the perlecan and glypican classes carry and bear HS chains almost exclusively, the syndecan core proteins are capable of carrying both HS and CS chains extracellularly. The appearance of specific glycosaminoglycan chains (such as HS and/or CS) extracellularly on protein cores is regulated both by the structure of the particular core protein as well as via the function of the Golgi apparatus intracellularly in a cell-type specific manner [Shworak et al., *J. Biol. Chem.* 269: 21204–21214 (1994)].

Today, it is recognized that the syndecan class is composed of four closely related family proteins (syndecan-1,-2,-3 and -4 respectively) coded for by four different genes in-vivo. Syndecans-1 and -4 are the most widely studied members of this class and show expression in a variety of different cell types including epithelial, endothelial, and vascular smooth muscle cells, although expression in quiescent tissues is at a fairly low level [Bernfield et al., *Annu. Rev. Cell Biol.* 8: 365–393 (1992); Kim et al., *Mol. Biol. Cell* 5: 797–805 (1994)]. Syndecan-2 (also known as fibroglycan) is expressed at high levels in cultured lung and skin fibroblasts, although immunocytochemically this core protein is barely detectable in most adult tissues. However, syndecan-3 (also known as N-syndecan) demonstrates a much more limited pattern of expression, being largely restricted to peripheral nerves and central nervous system tissues (although high levels of expression are shown in the neonatal heart) [Carey et al., *J. Cell Biol.* 117: 191–201 (1992)]. All four members of the syndecan class are capable of carrying both HS and CS chains extracellularly, although most of syndecan-associated biological effects (including regulation of blood coagulation, cell adhesion, and signal transduction) are largely thought to be due to the presence of HS chains capable of binding growth factors, or cell adhesion receptors and other biologically active molecules [Rosenberg et al., *J. Clin. Invest.* 99: 2062–2070 (1997)].

Syndecan-1 expression has been also observed during development suggesting a potential role in the epithelial organization of the embryonic ectoderm and in differential axial patterning of the embryonic mesoderm, as well as in cell differentiation [Sutherland et al., *Development* 113: 339–351 (1991); Trautman et al., *Development* 111: 213–220 (1991)]. Also, mesenchymal cell growth during tooth organogenesis is associated with transient induction of syndecan-1 gene expression [Vainio et al., *Dev. Biol.* 147: 322–333 (1991)]. Furthermore, in adult living tissues, expression of syndecan-1 and syndecan-4 proteoglycans substantially increases within arterial smooth muscle cells after balloon catheter injury [Nikkari et al., *Am. J. Pathol.* 144: 1348–1356 (1994)]; in healing skin wounds [Gallo et al., *Proc. Natl. Acad. Sci. USA* 91: 11035–11039 (1994)]; and in the heart following myocardial infarction [Li et al., *Circ. Res.* 81: 785–796 (1997)]. In the latter instances, the presence of blood-derived macrophages appears necessary for the induction of syndecan-1 and -4 gene expression.

Presently, however, the effects of changes in syndecan expression on cell behavior are not well understood. For example, this core protein is believed to mediate bFGF binding and cell activity. Overexpression of syndecan-1 in 3T3 cells led to inhibition of bFGF-induced growth [Mali et al., *J. Biol. Chem.* 268: 24215–24222 (1993)]; while in 293T cells, overexpression of syndecan-1 augmented serum-dependent growth [Numa et al., *Cancer Res.* 55: 4676–4680 (1995)]. Furthermore, syndecan-1 overexpression showed increased inter-cellular adhesion in lymphoid cells [Lebakken et al., *J. Cell Biol.* 132: 1209–1221 (1996)] while also decreasing the ability of B-lymphocytes to invade collagen gels [Liebersbach, B. F. and R. D. Sanderson, *J. Biol. Chem.* 269: 20013–20019(1994)]. These ostensibly contradictory findings have merely added to the uncertainty and the disparity of knowledge regarding the effects of syndecan expression.

In addition, although there are significant differences between the sequences of their ectoplasmic domains, the four syndecans share a highly conserved cytoplasmic tail containing four invariant tyrosines and one invariant serine [Kojima et al., *J. Biol. Chem.* 267: 4870–4877 (1992)]. This degree of conservation may reflect functional similarities between cytoplasmic tails of all the syndecans. However, unlike the well established involvement of the ectoplasmic domain in growth factor binding through the GAG chains, there is still no consensus regarding the function of the cytoplasmic tail. Several reports [Carey et al., *J. Cell Biol.* 124: 161–170 (1994); Carey et al., *Exp. Cell Res.* 214: 12–21 (1994)] point to transient association of the cytoplasmic tail of syndecan-1 to the actin cytoskeleton which seems to be highly dependent on the presence of one of the four conserved tyrosines [Carey et al., *J. Biol. Chem.* 271: 15253–15260 (1996)].

It is recognized also that the 18-amino acid-long cytoplasmic tail of syndecan-4 is the least homologous to the other three syndecans, containing a unique nine-residue sequence (RMKKKDEGSYDLGKKPIYKKAPTNEFYA) (SEQ I.D. NO: 1). Syndecan-4 is incorporated into focal adhesions of fibroblasts in a PKC-dependent manner [Baciu, P. C. and P. F. Goetinck, *Mol. Biol. Cell* 6: 1503–1513 (1995)]; and its cytoplasmic tail appears to bind and activate PKCα [Oh et al., *J. Biol. Chem.* 272: 8133–8136 (1997)]. These capacities are special to the cytoplasmic tail of syndecan-4 and not shared by the other syndecans, because they are mediated through oligomerization of its unique nine-residue sequence [Oh et al., *J. Biol. Chem.* 272: 11805–11811 (1997)].

Also, the presence of the five conserved phosphorylatable residues in the cytoplasmic tails of all the syndecans has been noted. However, although in-vitro phosphorylation by calcium-dependent PKC of serine residues in partial or complete synthetic cytoplasmic tails was reported for syndecan-2 and syndecan-3, it could not be produced for syndecan-1 or syndecan-4 [Prasthofer et al., *Biochem. Mol. Biol. Int.* 36: 793–802 (1995); Oh et al., *Arch. Biochem. Bio Phys.* 344: 67–74 (1997)]. Serine phosphorylation in situ was detected in syndecan-2 of carcinoma cells cultured in the presence of serum [Itano et al., *Biochem. J.* 325: 925–930 (1996)]. This phosphorylation was attributed to the serine residue in the cytoplasmic tail of syndecan-2, contained within a sequence that conforms to a phosphorylation motif of cAMP and cGMP-dependent kinases. In situ phosphorylation of the cytoplasmic tail of syndecan-1 was produced in mammary gland cells by treatment with orthoyanadate or pervanadate, both of which inhibit tyrosine phosphatase [Reiland et al., *Biochem. J.* 319: 39–47 (1996)]. Accordingly, this treatment resulted predominantly in tyrosine phosphorylation, although a lesser degree of serine phosphorylation was also detected. One of the four tyrosines in the cytoplasmic tail of syndecan-1 is contained within a tyrosine kinase phosphorylation motif [Gould et al., *Proc. Natl. Acad. Sci. USA* 89: 3271–3275 (1992)] conserved in all the syndecans and may at least partially account for the orthovanadate and pervanadate-produced phosphorylation.

In sum therefore, it is evident that the quantity and quality of knowledge presently available regarding glycoseaminoglycan (GAG) binding core proteins is factually incomplete, often presumptive, and in some instance apparently contradictory. Clearly the role of specific proteoglycans, and particularly syndecans, as mediators under various conditions is recognized; nevertheless, the mechanisms of action and the functional activity of the various individual syndecan core proteins remains yet to be elucidated. Thus, while the role of proteoglycans generally is known to relate in some manner to angiogenesis, there is no evidence or data as yet which establishes the true functional action of specific proteoglycans nor which provides a means for using specific proteoglycans to stimulate angiogenesis in-situ.

SUMMARY OF THE INVENTION

The present invention is comprised of related alternatives and has multiple aspects. One aspect provides a first method for stimulating angiogenesis within various tissues and organs in-situ, said method comprising:

identifying a viable endothelial cell in-situ as a target, said targeted endothelial cell bearing a plurality of transmembrane syndecan-4 proteoglycans positioned at and through the cell surface wherein the 183rd amino acid residue present within the intracellular cytoplasmic domain of said syndecan-4 proteoglycan is a serine residue;

administering to said targeted endothelial cell on at least one occasion a predetermined amount of an inhibitor of Protein Kinase C δ (delta) isoenzyme activity such that said 183rd serine residue within the cytoplasmic domain of at least some of said syndecan-4 proteoglycans is present in a non-phosphorylated state; and allowing said 183rd serine residue within the cytoplasmic domain of said syndecan-4 proteoglycans to continue to be present in a non-phosphorylated state, whereby a stimulation of angiogenesis in-situ results. Another aspect provides a related, but alternative method for stimulating angiogenesis within viable cells, tissues, and organs in-situ, said alternative method comprising:

identifying a viable endothelial cell in-situ as a target, said targeted endothelial cell bearing a plurality of transmembrane syndecan-4 proteoglycans positioned at and through the cell surface wherein the 183rd amino acid residue present within the intracellular cytoplasmic domain of said syndecan-4 proteoglycan is a serine residue;

administering to said targeted endothelial cell on at least one occasion a predetermined amount of a composition able to increase Protein Kinase C α (alpha) isoenzyme activity intracellularly such that said 183rd serine residue within the cytoplasmic domain of at least some of said syndecan-4 proteoglycans is present in an non-phosphorylated state in-situ; and allowing said 183rd serine residue within the cytoplasmic domain of said syndecan-4 proteoglycans to continue to be present in a non-phosphorylated state, whereby a stimulation of angiogenesis in-situ results.

A different aspects provides another related, but alternative method for stimulating angiogenesis within viable cells, tissues, and organs in-situ, said alternative method comprising:

identifying a viable endothelial cell in-situ as a target, said targeted endothelial cell bearing a plurality of transmembrane syndecan-4 proteoglycans positioned at and through the cell surface wherein the 183rd amino acid residue present within the intracellular cytoplasmic domain of said syndecan-4 proteoglycan is a serine residue;

administering to said targeted endothelial cell on at least one occasion a predetermined amount of an substance able to activate at least one enzyme selected from the group consisting of protein phosphatases 1 and 2A such that said 183rd serine residue within the cytoplasmic domain of at least some of said syndecan-4 proteoglycans is present in an non-phosphorylated state; and allowing said 183rd serine residue within the cytoplasmic domain of said syndecan-4 proteoglycans to continue to be present in a non-phosphorylated state, whereby a stimulation of angiogenesis in-situ results.

BRIEF DESCRIPTION OF THE FIGURES

The present invention may be more easily understood and better appreciated when taken in conjunction with the accompanying drawing, in which:

FIGS. 8A–8D are graphs showing the results of size-exclusion column chromatography of syndecan-4 cytoplasmic tail peptides.

DETAILED DESCRIPTION OF THE INVENTION

Figure 1A:
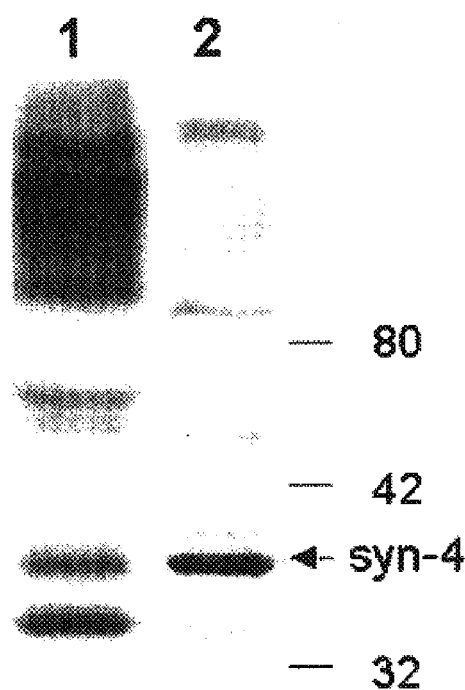
FIGS. 1A and 1B are photographs showing the detection of syndecan-4 core protein basal phosphorylation and identification of serine phosphorylation.

The present invention provides both tangible means and methods for causing the 183rd residue, serine, in the cytoplasmic domain of syndecan-4 core proteins of vascular endothelial cells to exist in a non-phosphorylated state in-situ; and by this intervention and meaningful change, consequentially to effect a stimulation of angiogenesis at the local anatomic site in-vivo.

A number of major benefits and advantages are therefore provided by the means and methods comprising the present invention. These include the following:

1. The present invention provides in-situ stimulation for angiogenesis. By definition, therefore, both in-vivo and in-vitro circumstances of use and application are envisioned and expected. Moreover, the vascular endothelial cells which are suitable for treatment using the present methods may alternatively include and be isolated endothelial cells, part of living tissues comprising a variety of other cells such as fibroblasts and muscle cells, and also comprise part of specific organs in the body of a living human or animal subject. While the user shall choose the specific conditions and circumstances for practicing the present invention, the intended scope of application and the envisioned utility of the means and methods described herein apply broadly to living cells, living tissues, functional organs and systems, as well as the complete living body unit as a viable whole.

2. The present invention has a variety of different applications and uses. Of clinical and medical interest and value, the present invention provides the opportunity to stimulate angiogenesis in tissues and organs in a living subject which has suffered defects or has undergone anoxia or infarction. A common clinical instance is the myocardial infarction or chronic myocardial ischemia of heart tissue in various zones or areas of a living human subject. The present invention thus provides opportunity and means for specific site stimulation and inducement of angiogenesis under controlled conditions. The present invention also has major research value for research investigators in furthering the quality and quantity of knowledge regarding the mechanisms controlling angiogenesis under a variety of different conditions and circumstances.

3. The present invention envisions and permits a diverse range of routes of administration and delivery means for introducing a variety of synthetically constructed oligonucleotide expression vectors to a specific location, site, tissue, organ, or system in the living body. A variety of different vectors are available to the practitioner; and a diverse and useful range of delivery systems which are conventionally available and in accordance with good medical practice are adapted directly for use. In this manner, not only are the means for stimulating angiogenesis under the control of the user, but also the manner of application and the means for limiting the locale or area of affected vascular endothelial cells can be chosen and controlled.

4. The present invention provides a unique capability and control for stimulating angiogenesis in-situ by genetic manipulation of the endothelial cells as they exist within the tissues and organs as found. This level of control and utilization of the mechanisms found within the cytoplasms of the endothelial cells themselves provides a point of intentional intervention which harnesses and utilizes the cellular systems of the endothelial cells themselves to produce the intended and desired result. The affected endothelial cells in-situ are thus minimally altered; and the methodology utilizes the natural regulatory and protein producing systems of the endothelial cells themselves to provide the desired effect upon syndecan-4 proteoglycans which are located and positioned normally by the endothelial cells as part of the normal homeostatic mechanisms.

I. Underlying Basis Of The Invention

Recent research investigations have shown that a member of the syndecan family of heparan sulfate-carrying proteoglycans participates in intracellular signalling via its cytoplasmic tail. This particular transmembrane proteoglycan, syndecan-4, is a ubiquitous molecule present in-vivo within most human cells and tissues, including the vascular endothelium. The present invention utilizes and takes advantage of syndecan-4's cellular function in order to control and upregulate new blood vessel growth and to promote angiogenesis, particularly in the heart.

The underlying premise of the present invention is that phosphorylation of the cytoplasmic tail of syndecan-4 at the $Ser^{183}$ residue regulates a member of the protein kinase C enzyme family (PKCα), whose specific enzymatic activity is essential for proliferation and migration of endothelial cells in-vivo. As empirically demonstrated, the $Ser^{183}$ dephosphorylated residue in the syndecan-4 molecule can significantly increase the catalytic activity of PKCα, while the phosphorylated $Ser^{183}$ residue form of syndecan-4 merely activates PKCα. This result and effect is empirically proven by the experiments and data presented hereinafter. Thus, by inhibiting the Protein Kinase C isoenzyme responsible for $Ser^{183}$ phosphorylation, and/or by activating the corresponding phosphatase that removes the phosphate group from the $Ser^{183}$ residue, the means now exist to increase PKCα activity, and to promote endothelial cell proliferation and migration in-situ.

Several lines of evidence further reveal the relation between the phosphorylation level of the syndecan-4 cytoplasmic domain and its associated effects on PKCα, and the consequential proliferation and migration activities of endothelial cells. First and foremost, a significant decrease in syndecan-4 phosphorylation is observed upon cell treatment with bFGF. Thus, the occurrence of syndecan-4 dephosphorylation in the cytoplasmic tail region accompanies the proliferative response of the endothelial cells to one of the most ubiquitous growth factors, and one which is secreted in response to clinical ischemia and infarction. Second, it has only recently been observed that dephosphorylation of the cytoplasmic tail of syndecan-4 is required for its activation of PKCα. Thus, syndecan-4 phosphorylation is an event directly linked to a PKC isoenzyme which is known to promote endothelial cells migration. Third, empirical data indicate that endothelial cells, in which PKCα has been suppressed by transfection with an inactive form of enzyme kinase, proliferate at a much slower rate than wild type cells which have not been suppressed. Fourth, and finally, endothelial cells transfected with a syndecan-4 mutant bearing a $Ser^{183}$-$Glu^{183}$ replacement (which mimics the conferral of a negative charge by phosphorylation) also proliferated at a lower rate than wild type endothelial cells. Taken together, all these findings provide confirmation and evidentiary support for the role of syndecan4 cytoplasmic tail phosphorylation in endothelial cell migration and proliferation. Consequently, control and regulation of syndecan-4 cytoplasmic tail phosphorylation is a potent methodology suitable and effective as therapies aimed at promoting angiogenesis.

II. The Syndecan-4 Cytoplasmic Domain

It will be recalled that the 28 amino acid-long cytoplasmic tail of syndecan-4 is the least homologous to the other three syndecans, containing a unique nine amino acid residue sequence (shown in bold type) RMKKKDEGSY-DLGKKPIYKKAPTNEFYA [SEQ ID NO:1]

Syndecan-4 is known to be incorporated into focal adhesions of fibroblasts in a PKC-dependent manner and its cytoplasmic tail in the phosphorylated state binds and activates PKCα directly. These capacities and functions are special to the cytoplasmic tail of syndecan-4; and these capacities and functions are not shared by the other syndecans, since they are mediated through oligomerization of the syndecan-4 cytoplasmic tail's unique nine-residue sequence.

The critical and essential target of the present methods, therefore, is the serine residue located in-situ as the 183rd amino acid in the syndecan-4 molecular structure and existing in proximity to the unique nine amino acid residue sequence of the 28 residue-long cytoplasmic tail. This individual serine residue is the sole and exclusive site of interest; and it appears that no other individual amino acid residue and no peptide segment within the cytoplasmic domain is involved in any major degree.

Equally important, it will be recognized and appreciated that it is the state of this $serine^{183}$ residue—as being either non-phosphorylated or phosphorylated—which provides the invention with the means for and the effect of regulatory control. Thus, the larger the number of syndecan-4 core proteins whose intracellular cytoplasmic domain comprises an unphosphorylated serine[183] residue, the greater the upregulation of PKCα isoenzyme catalysis and the greater the inducement of angiogenesis in-situ. Conversely, the larger the number of syndecan-4 proteoglycans having a phosphorylated serine[183] residue as part of their intracellular cytoplasmic domains, the smaller the degree of PKCα isoenzyme catalysis and the more limited the amount of angiogenesis in-situ.

III. The Methodology Comprising The Present Invention

The goal and objective of the present invention is to prevent the phosphorylation of or to decrease the phosphorylation level of Ser[183] residue in the cytoplasmic domain or tail of syndecan-4 molecules then present and existing within vascular endothelial cells. The phosphorylation level of the Ser[183] residue is normally an outcome of a dynamic equilibrium between the catalytic activities of a pair of enzymes—of a specific protein kinase and a phosphatase that incorporate or remove, respectively, a phosphate group. These two enzymes are, therefore, the individual objects to be manipulated in a variety of modes. The categorical methods and goals of these manipulations thus are and include:

(A) Means and procedures to inhibit the protein kinase responsible for the phosphorylation of Ser[183] in the cytoplasmic tail of syndecan-4. This kinase has been identified and empirically shown to be the calcium-independent PKCδ (delta) isoenzyme.

(B) Means and procedures to increase PKCα (alpha) activity. The dephosphorylated cytoplasmic tail of syndecan-4 has been empirically shown to promote PKCα (alpha) activity, which directly increases the angiogenic potential of endothelial cells in-situ.

(C) Means and procedures to activate the phosphatase responsible for the dephosphorylation of the Ser[183] residue in-situ. Though the specific phosphatase has not been completely identified as yet, it belongs to and is part of the protein phosphatase type 1/2A family.

Composition Preparation And Manufacture

As a point of information also, it will be recognized and appreciated that in terms of preparing and using suitable inhibitory agents and compositions, it is important, if not essential, that the user be at least familiar with the many established procedures and conventionally known techniques for manipulating and modifying nucleotides and DNA (and RNA) fragments as well as the vectors to carry them which have been reported and are today widespread in use and application. Merely exemplifying the many authoritative texts and published articles presently available in the literature regarding genes, DNA nucleotide manipulation and the expression of proteins from manipulated DNA fragments are the following: *Gene Probes for Bacteria* (imacario and De Marcario, editors) Academic Press Inc., 1990; *Genetic Analysis, Principles Scope and Objectives* by John R. S. Ficham, Blackwell Science Ltd., 1994; *Recombinant DNA Methodology* II (Ray Wu, editor), Academic Press, 1995; *Molecular Cloning. A Laboratory Manual* (Maniatis, Fritsch, and Sambrook, editors), Cold Spring Harbor Laboratory, 1982; *PCR (Polymerase Chain Reaction)*. (Newton and Graham, editors), Bios Scientific Publishers, 1994; and the many references individually cited within each of these publications. All of these published texts are expressly incorporated by reference herein.

A. Inhibition of PKCS (delta) Isoenzyme Activity (A.1) Chemical PKC Inhibitory Compounds:

A vast array of chemical PKC inhibitors has been developed and is commercially available. Examplifying such inhibitors is staurosporine, a substance obtained from Streptomyces species. Others are listed below in Table I. However, most of these inhibitors are non-selective and equally potent against all types of PKC isoenzymes. One noted exception of the calcium-dependent PKC isoenzyme inhibitor is Gö 6976 [Martiny-Baron et al., *J. Biol. Chem.* 268: 9194–9197 (1993)]. In so far as is presently known, however, there is no specific chemical inhibitor of the calcium-independent PKC isoenzymes in general, or of the PKCδ (delta) isoenzyme itself. Nevertheless, an inhibition of PKCδ is desirable and can be achieved by using Chelerythrinc or one of the alternatives given below.

TABLE 1

Representative PKC Inhibitors

| Inhibitor | $IC_{50}$ (in $\mu M$) |
|---|---|
| Calphostin | 0.05 |
| Chelerythrine chloride | 0.66 |
| Gö 6976 | 0.008 |
| Autoinhibitory peptide | 15 |
| Staurosporine | 0.0007 |

(A.2) Overexpression of the Autoinhibitory Domain of PKCδ (delta) Isoenzyme:

The regulatory domain of all PKC isoenzymes contains a sequence motif similar to the consensus sequence found in most PKC substrates in which the Thr or Ser residue normally phosphorylated by PKC is replaced by an Ala residue. In the inactive state of the enzyme, this motif blocks the catalytic domain and prevents enzyme interaction with its potential substrates. Induced over-expression of the pseudosubstrate domain of PKCδ will therefore reduce the activity of this isoenzyme by competing with its cellular substrates. Moreover, the pseudosubstrate domain of PKCδ is sufficiently different from those of the other PKC isoenzymes so as not to interfere with their catalytic activity. The pseudosubstrate domain of PKCδ (delta) isoenzyme is provided by Table 2 below.

It will be recognized that the information of Table 2 is a reproduction in part from Nishikawa et al., *J. Biol. Chem.* 272: 952–960 (1997), the full text of which is expressly incorporated by reference herein.

TABLE 2

The Pseudosubstrate Domain of the PKCδ (delta) Isoenzyme

| AARKRKGSFFYGG | [SEQ ID NO: 2] |
|---|---|

Over-expression of the PKCδ pseudosubstrate can be produced within the endothelial cell at the target region by transfection with the adenovirus containing a cDNA construct with the PKCδ pseudosubstrate sequence of Table 2. An established protocol and procedural detail has been reported and published in the scientific literature by Nishikawa et al., *J. Biol. Chem.* 272: 952–960 (1997); the text of this publication and its cited references is expressly incorporated by reference herein. The prepared adenovirus vector carrying the inserted DNA coding for the pseudosubstrate domain of the PKCδ (delta) isoenzyme can be administered by direct injection or infusion to the local anatomic site of the host in-vivo over a schedule dose administration over a period of days.

(A.3) Expression of PKCδ Anti-sense Constructs

Transfection with the anti-sense CDNA of a protein is a frequently used method for suppressing the expression of that protein. The mRNA transcribed from the transfected cDNA shuts off the translation of the target protein by hybridizing to the sense endogenous mRNA message. The delivery method of the anti-sense cDNA is similar to the one used above for over-expressing the pseudosubstrate domain of PKCδ, preferably also using the adenovirus vector for administration.

As a representative specific example of an antisense entity useful with the present invention, the PKCδ (delta) antisense sequences (I) and (II) are given below.

(I) PKC Delta antisense primer (42 mer):

5'-GGC CGC TGG GCA TCG AAC GTC GAC TTC CAC TCA GGA TAC ATG-3' [SEQ ID NO:3]

(II) PKC Delta antisense complement primer (42 mer):

5'-GAT CCA TGT ATC CTG AGT GGA AGT CGA CGT TCG ATG CCC AGC-3' [SEQ ID NO:4]

It will be recognized and appreciated that these two embodiments are merely representative and illustrative of this type of inhibitory compound; and that a wide range of other DNA oligonucleotide fragments can be prepared which will be useful and functional in varying degrees of efficacy.

(A.4) Delivery of Anti-sense Oligodeoxynucleotides (ODN)

In this approach, a short (around 15–30 base pairs) ODN with an anti-sense sequence corresponding to a chosen sequence in the cDNA of the protein intended for suppression is introduced in the target cells. The principle of this method is similar to that of the anti-sense construct, but instead of interfering with translation of the mRNA, this approach interferes with transcription by hybridization between of exogenous anti-sense ODN to the corresponding locus in the genomic DNA.

B. Increases in PKCα (alpha) Isoenzyme Activity (B.1) Chemically Induced Increases in PKCα Activity In addition to enhancing PKCα activity through prevention of syndecan-4 cytoplasmic tail phosphorylation, this PKCα activity can be increased directly. The commonly used compounds for increasing PKC activity are phorbol esters, but these compositions are not isoenzyme-specific. A representative listing of useful phorbol esters and other PKC activators, all of which are commercially available, is provided by Table 3 below. In addition, however, an increase in PKC activity limited to the α (alpha) isoenzyme can be achieved using one of the alternative methods described below.

TABLE 3

Representative Phorbol Ester Compositions

ADMB;
Ingenol;
1,2-Didecanoyl-rac-glycerol-Mezerein;
Phorbol-12-myristate-13-acetate (PMA);
1-stearoyl-2-arachidonoyl-SN-glycerol;
12-0-tetradecanoyl-phorbol-13-acetate (TPA)

(B.2) Over-expression of Full-length PKCα Molecules

A marked increase in the number and abundance of PKCα (alpha) isoenzyme molecules will elevate the phosphorylation level of its downstream substrates, resulting in higher proliferative and migratory cellular activities. Such increase can be achieved by introducing exogenous cDNA encoding the full-length PKCα (alpha) isoenzyme using adenoviral transfection as conventionally known and practiced. For ease of understanding and completeness of description, a recitation of cDNA encoding the entirety of the PKCα (alpha) isoenzyme is provided by Table 4 below.

In addition, the cDNA recitation of Table 4 will be recognized as a reproduction in-part of the scientific information published in Parker et al., *Science* 233: 853–859 (1986), the full text of which is expressly incorporated by reference herein.

TABLE 4 cDNA Encoding the PKCα (alpha) Isoenzyme

| | | |
|---|---|---|
| LOCUS | BOVPKIC    2324 bp    mRNA    MAM    08-APR-1987 | |
| DEFINITION | Bovine protein kinase C mRNA, complete cds. | |
| ACCESSION | M13973 | |
| NID | g163529 | |
| KEYWORDS | kinase; phorbol ester receptor; protein kinase; protein kinase C; serine kinase; threonine kinase. | |
| SOURCE | Bovine (calf) brain, cDNA to mRNA, clones lambda-bPKC[21,306]. | |
| ORGANISM | *Bos taurus*<br>Eukaryotae; mitochondrial eukaryotes; Metazoa; Chordata; Vertebrata; Eutheria; Artiodactyla; Ruminantia; Pecora; Bovoidea; Bovidae; Bovinae; Bos. | |
| REFERENCE | 1 (bases 1 to 2324) | |
| AUTHORS | Parker, P. J., Coussens, L., Totty, N. F., Rhee, L., Young, S., Chen, E., Stabel, S., Waterfield, M. D. and Ullrich, A. | |
| TITLE | The complete primary structure of protein kinase C-the major phorbol ester receptor | |
| JOURNAL | Science 233, 853–859 (1986) | |
| MEDLINE | 86289425 | |
| FEATURES | Location/Qualifiers | |
| source | 1 . . . 2324<br>/organism="*Bos taurus*"<br>/db_xref="taxon:9913" | |
| mRNA | <1 . . . >2324<br>/note="pkC mRNA" | |
| CDS | 51 . . . 2069 | |

TABLE 4-continued cDNA Encoding the PKCα (alpha) Isoenzyme

```
            /note="protein kinase C"
            /codon_start=1
            /db_xref="PID:g163530"
            /translation="MADVFPAAEPAAPQDVANRFARKGALRQKNVHEVKNHRFIARFF
            KQPTFCSHCTDFIWGFGKQGFQCQVCCFVVHKRCHEFVTFSCPGADKGPDTDDPRSKH
            KFKIHTYGSPTFCDHCGSLLYGLIHQGMKCDTCDMNVHKQCVINVPSLCGMDHTEKRG
            RIYLKAEVTDEKLHVTVRDAKNLIPMDPNGLSDPYVKLKLIPDPKNESKQKTKTIRST
            LNPRWDESFTFKLKPSDKDRRLSEEIWDWDRTTRNDFMGSLSFGVSELMKMPASGWYK
            LLNQEEGEYYNVPIPEGDEEGNVELRQKFEKAKLGPAGNKVISPSEDRRQPSNNLDRV
            KLTDFNFLMVLGKGSFGKVMLADRKGTEELYAIKILKKDVVIQDDDVECTMVEKRVLA
            LLDKPPFLTQLHSCFQTVDRLYFVMEYVNGGDLMYHIQQVGKFKEPQAVFYAAEISIG
            LFFLHKRGIIYRDLKLDNVMLDSEGHIKIADFGMCKEHMMDGVTTRTFCGTPDYIAPE
            IIAYQPYGKSVDWWAYGVLLYEMLAGQPPFDGEDEDELFQSIMEHNVSYPKSLSKEAV
            SICKGLMTKHPGKRLGCGPEGERDVREHAFFRRLDWEKLENREIQPPFKPKVCGKGAE
            NFDKFFTRGQPVLTPPDQLVIANIDQSDFEGFSYVNPQFVHPILQSAV" [SEQ ID NO:5]
BASE COUNT      527 a      683 c      695 g      419 t
ORIGIN     201 bp upstream of PstI site.
    1      ccctctcggc cgccgcccgc gcccccccgcg gcaggaggcg gcgagggacc atggctgacg
   61      tcttcccggc cgccgagccg gcggcgccgc aggacgtggc caaccgcttc gcccgcaaag
  121      gggcgctgag gcagaagaac gtgcacgagg tgaagaacca ccgcttcatc gcgcgcttct
  181      tcaagcagcc caccttctgc agccactgca ccgacttcat ctgggggttt gggaaacaag
  241      gcttccagtg ccaagtttgc tgttttgtgg ttcacaagag gtgccatgaa tttgttactt
  301      tttcttgtcc gggggcggat aaaggacccg aacagatga cccgaggagc aagcacaagt
  361      tcaagatcca cacgtatggc agccccacct tctgtgatca ctgcggctcc ctgctctacg
  421      gactcatcca ccaggggatg aaatgtgaca cctgtgatat gaacgtgcac aagcagtgcg
  481      tgatcaacgt gcccagcctc tgcgggatgg accacacgga gaagagggc cgcatctacc
  541      tgaaggccga ggtcacggat gaaaagctgc acgtcacagt acgagacgcg aaaaacctaa
  601      tccctatgga tccaaatggg ctttcagatc cttacgtgaa gctgaagctt attcctgacc
  661      ccaagaacga gagcaaacag aaaaccaaga ccatccgctc gacgctgaac cccggtgggg
  721      acgagtcctt cacgttcaaa ttaaaacctt ctgataaaga ccggcgactg tccgaggaaa
  781      tctgggactg ggatcgaacc acacggaacg acttcatggg gtcccttttcc tttggggtct
  841      cggagctgat gaagatgccg gccagcggat ggtacaagct gctgaaccaa gaggagggcg
  901      agtactacaa cgtgccgatc cccgaaggcg acgaggaagg caatgtggag ctcaggcaga
  961      aattcgagaa agccaagctt ggccctgccg gcaacaaagt catcagtccc tccgaggaca
 1021      ggagacagcc ttccaacaac ctggacagag tgaagctcac ggacttcaac ttcctcatgg
 1081      tgctgggcaa aggcagcttt gggaaggtga tgctggccga ccggaagggg acagaggagc
 1141      tgtacgccat caagatcctg aagaaggacg tggtcatcca ggacgacgac gtggagtgca
 1201      ccatggtgga gaagcgggtc ctggcgctgc tcgacaagcc gccgttcctg acgcagctgc
 1261      actcctgctt ccagacggtg gaccggctgt acttcgtcat ggagtacgtc aacggcgggg
 1321      acctcatgta ccacatccag caggtcggga agttcaagga gccgcaagca gtgttctatg
 1381      cagcagagat ttccatcggg ctgttctttc ttcataaaag aggaatcatt tatcgggacc
 1441      tgaagttaga caacgtcatg ctggactcgg aaggacacat taagatcgcg gacttcggga
 1501      tgtgcaagga gcacatgatg gacggcgtca cgaccaggac cttctgcggg acccccgact
 1561      acatcgcccc agagataatc gcctatcagc cgtacgggaa gtccgtcgac tggtgggcct
 1621      acggcgtcct gttgtacgag atgttggccg ggcagcctcc gttcgacggc gaggacgagg
 1681      acgagctgtt ccagtccatc atggagcaca acgtctcgta ccccaagtcc ttgtccaagg
 1741      aggccgtgtc catctgcaaa gggctgatga ccaagcaccc cgggaagcgg ctgggctgcg
 1801      ggcccgaggg cgagcgcgac gtgcgggagc atgccttctt ccggaggatc gactgggaga
 1861      agctggagaa ccgtgagatc cagccaccct tcaagcccaa agtgtgcggc aaaggagcag
 1921      agaactttga caagttcttc acgcgagggc agcctgtctt gacgccgccc gaccagctgg
 1981      tcatcgctaa catcgaccag tctgattttg aaggcttctc ctacgtcaac ccccagttcg
 2041      tgcaccccat cctgcagagc gcggtatgag acgcctcgcg gaagcctggt ccgcgccccc
 2101      gccccgcct ccgcccccgc cgtgggaagc gaccccacc ctagggtttg ccggcctcgg
 2161      ccctccctgt tccaggtgga ggcctgaaaa ctgtagggtg gttgtccccg cgtgctcggc
 2221      tgcgtcatct cagcggaaga tgacgtcacg tcggcatctg cttgacgtag aggtgacatc
 2281      tggcggggga ttgacccttt ctggaaagca aacagactct ggcc [SEQ ID NO:6]
```

(B. 3) Over-expression of PKCα Catalytic Domain

A larger increase in PKCα activity can be achieved by over-expressing only the cDNA encoding its unregulated catalytic subunit (PKM), instead of the full-length protein. The catalytic subunit (PKM) is constitutively active in and of itself; and will increase the basal activity of PKCα when introduced to a viable cell even in the absence of external activation. A recitation of the cDNA encoding the catalytic subunit (PKM) alone of the PKCα (alpha) isoenzyme is provided by Table 5 below. It will be appreciated that the recitation of Table 5 is a reproduction in part of the information presented by Parker et al., *Science* 233: 853–859 (1986), the full text of which is expressly incorporated by reference herein.

TABLE 5 cDNA Encoding the Catalytic Subunit (PKM) of PKCα (alpha) Isoenzyme

```
acggacttca acttcctcat ggtgctgggc aaaggcagct ttgggaaggt gatgctggcc
gaccggaagg ggacagagga gctgtacgcc atcaagatcc tgaagaagga cgtggtcatc
```

TABLE 5-continued cDNA Encoding the Catalytic Subunit (PKM) of PKCα (alpha) Isoenzyme

```
caggacgacg acgtggagtg caccatggtg gagaagcggg tcctggcgct gctcgacaag
ccgccgttcc tgacgcagct gcactcctgc ttccagacgg tggaccggct gtacttcgtc
atggagtacg tcaacggcgg ggacctcatg taccacatcc agcaggtcgg gaagttcaag
gagccgcaag cagtgttcta tgcagcagag atttccatcg ggctgttctt tcttcataaa
agaggaatca tttatcggga cctgaagtta gacaacgtca tgctggactc ggaaggacac
attaagatcg cggacttcgg gatgtgcaag gagcacatga tggacggcgt cacgaccagg
accttctgcg ggacccccga ctacatcgcc ccagagataa tcgcctatca gccgtacggg
aagtccgtgg actggtgggc ctacggcgtc ctgttgtacg agatgttggc cgggcagcct
ccgttcgacg gcgaggacga ggacgagctg ttccagtcca tcatggagca caacgtctcg
taccccaagt ccttgtccaa ggaggccgtg tccatctgca aagggctgat gaccaagcac
cccgggaagc ggctgggctg cgggcccgag ggcgagcgcg acgtgcggga gcatgccttc
ttccggagga tc [SEQ ID NO:7]
```

C. Activation of Protein Phosphatase 1/2A

As noted previously herein, the field of phosphatases responsible for dephosphorylating the $Ser^{183}$ in the cytoplasmic tail of syndecan-4 in-situ has been narrowed markedly to protein phosphatase type 1 (PP1) or 2A (PP2A). This fact has been experimentally verified hereinafter.

In addition, the capacity of okadaic acid to inhibit the dephosphorylation of the cytoplasmic tail of syndecan-4 is being employed to discriminate between the two enzyme types. Since protein phosphatase PP2A is more sensitive to okadaic acid than type PP1 enzyme, these experiments will serve to discriminate between the two enzyme types. After the phosphatase type is determined and precisely identified, the following procedures can be used to increase phosphatase enzyme activity in the target cell population:

(C1) Over-expression of the Catalytic Subunits of the Protein Phosphatase

Protein phosphatase type PP1 is a multimer consisting of a catalytic subunit and one of several known inhibitory subunits [Mumby, M. C. and G. Walter, *Physiol. Rev.* 73: 673–699 (1993)]. In comparison, protein phosphatase type PP2A is a heterotrimer of two regulatory subunits (A and B) and a catalytic subunit (C). Once it has been determined whether type PP1 or type PP2A is responsible for dephosphorylating the cytoplasmic tail of syndecan-4, the respective catalytic subunit can be over-expressed by adenoviral transfection with the cDNA of this subunit. For informational purposes, the DNA sequence for both types PP1 and PP2A is provided by Table 6 below.

TABLE 6

```
LOCUS       HUMPRPHOS1   1367 bp    mRNA              PRI         22-APR-1991
DEFINITION  Human protein phosphatase-1 catalytic subunit mRNA, complete cds.
ACCESSION   M63960
NID         g190515
KEYWORDS    dephosphorylate phosphoprotein; protein phosphatase-1.
SOURCE      Human liver hepatoma Hep G2 cell line, cDNA to mRNA, clone
            PP1HEPG2-B.
ORGANISM    Homo sapiens
            Eukaryotae; mitochondrial eukaryotes; Metazoa; Chordata;
            Vertebrata; Eutheria; Primates; Catarrhini; Hominidae; Homo.
REFERENCE   1 (bases 1 to 1367)
AUTHORS     Tung, L.
JOURNAL     Unpublished (1991)
FEATURES            Location Qualifiers
    source          1 . . . 1367
                    /organism="Homo sapiens"
                    /db_xref="taxon:9606"
                    /cell_line="Hep G2"
                    /cell_type="hepatoma"
                    /tissue_type="liver"
                    /tissue_lib="Hep G2 cDNA library"
    CDS             30 . . . 1022
                    /EC_number="3.1.3.16"
                    /note="catalytic subunit"
                    /codon_start=1
                    /product="protein phosphatase-1"
                    /db_xref="PID:g190516"
                    /translation="MSDSEKLNLDSIIGRLLEVQGSRPGKNVQLTENEIRGLCLKSRE
                    IFLSQPILLELEAPLKICGDIHGQYYDLLRLFEYGGFPPESNYLFLGDYVDRGKQSLE
                    TICLLLAYKIKYPENFFLLRGNHECASINRIYGFYDECKRRYNIKLWKTFTDCFNCLP
                    IAAIVDEKIFCCHGGLSPDLQSMEQIRRIMRPTDVPDQGLLCDLLWSDPDKDVQGWGE
                    NDRGVSFTFGAEVVAKFLHKHDLDLICRAHQVVEDGYEFFAKRQLVTLFSAPNYCGEF
                    DNAGAMMSVDETLMCSFQILKPADKNKGKYGQFSGLNPGGRPITPPRNSAKAKK"
                    [SEQ ID NO:8]
BASE COUNT     288 a     400 c    393 g    286 t
ORIGIN
     1    gggcaaggag ctgctggctg gacggcggca tgtccgacag cgagaagctc aacctggact
    61    cgatcatcgg gcgcctgctg gaagtgcagg gctcgcggcc tggcaagaat gtacagctga
```

TABLE 6-continued

```
  121       cagagaacga gatccgcggt ctgtgcctga aatcccggga gattttctg agccagccca
  181       ttcttctgga gctggaggca cccctcaaga tctgcggtga catacacggc cagtactacg
  241       accttctgcg actatttgag tatggcggtt tccctcccga gagcaactac ctctttctgg
  301       gggactatgt ggacaggggc aagcagtcct tggagaccat ctgcctgctg ctggcctata
  361       agatcaagta ccccgagaac ttcttcctgc tccgtgggaa ccacgagtgt gccagcatca
  421       accgcatcta tggttttctac gatgagtgca agagacgcta acatcaaa ctgtggaaaa
  481       ccttcactga ctgcttcaac tgcctgccca tcgcggccat agtggacgaa aagatcttct
  541       gctgccacgg aggcctgtcc ccggacctgc agtctatgga gcagattcgg cggatcatgc
  601       ggcccacaga tgtgcctgac cagggcctgc tgtgtgacct gctgtggtct gaccctgaca
  661       aggacgtgca gggctgggc gagaacgacc gtggcgtctc tttaccttt ggagccgagg
  721       tggtggccaa gttcctccaa aagcacgact tggacctcat ctgccgagca caccaggtgg
  781       tagaagacgg ctatgagttc tttgccaagc ggcagctggt gacacttttc tcagctccca
  841       actactgtgg cgagtttgac aatgctggcg ccatgatgag tgtggacgag accctcatgt
  901       gctctttcca gatcctcaag cccgccgaca gaacaaggg gaagtacggg cagttcagtg
  961       gcctgaaccc tggaggccga cccatcaccc caccccgcaa ttccgccaaa gccaagaaat
 1021       agccccgca caccacctg tgcccagat gatggattga ttgtacagaa atcatgctgc
 1081       catgctgggg ggggtcacc ccgaccccta aggcccacct gtcacgggga acatggagcc
 1141       ttggtgtatt tttcttttct tttttaatg aatcaatagc agcgtccagt cccccagggc
 1201       tgcttcctgc ctgcaccctgc ggtactgtga gcaggatcct ggggccgagg ctgcagctca
 1261       gggcaacggc aggccaggtc gtgggtctcc agccgtgctt ggcctcaggc tggcagcccg
 1321       gatcctgggg caacccatct ggtctcttga ataaaggtca aagctg [SEQ ID NO:9]
LOCUS       BOVPHO2A    1721 bp    mRNA           MAM      15-JUN-1988
DEFINITION  Bovine protein phosphatase type 2A catalytic subunit mRNA, complete
            cos,
ACCESSION   M16968
NID         g163515
KEYWORDS    phosphoprotein phosphatase 2A.
SOURCE      Bovine adrenal, cDNA to mRNA, clone pPBC-1.
ORGANISM    Bos taurus
            Eukaryotae; mitochondrial eukaryotes; Metazoa; Chordata;
            Vertebrata; Eutheria; Artiodactyia; Ruminantia; Pecora; Bovoidea;
            Bovidae; Bovinae; Bos.
REFERENCE   1 (bases 1 to 1721)
AUTHORS     Green, D. D., Yang, S. -I. and Mumby, M. C.
TITLE       Molecular cloning and sequence analysis of the catalytic subunit of
            bovine type 2A protein phosphatase
JOURNAL     Proc. Natl. Acad. Sci. U.S.A. 84, 4880-4884 (1987)
MEDLINE     87260892
COMMENT     Draft entry and printed copy of sequence for [1] kindly provided by
            M. C. Mumby, 09-SEP-1987.
FEATURES            Location/Qualifiers
     source         1 . . . 1721
                    /organism="Bos taurus"
                    /db_xref="taxon:9913"
     mRNA           <1 . . . 1721
                    /note="PP-C mRNA"
     CDS            104 . . . 1081
                    /note="protein phosphatase type 2A catalytic subunit"
                    /codon_start=1
                    /db_xref="PID:g163516"
                    /translation="MDEKVFTKELDQWIEQLNECKQLSESQVKSLCRRLKKSWTKESN
                    VQEVRCPVTVRGDVHGQFHDLMELFRIGGKSPDTNYLFMGDYVDRGYYSVETVTLLVA
                    LKVRYRERITILRGNHESRQITQVYGFYDECLRKYGNANVWKYFTDLFDYLPLTALVD
                    GQIFCLHGGLSPSIDTLDHIRALDRLQEVPHEGPMCDLLWSDPDDRGGWGISPRGAGY
                    TFGQDISETFNHANGLTLVSRAHQLVMEGYNWCHDRNVVTIFSAPNYCYRCGNQAAIM
                    ELDDTLKYSFLQFDPAPAEASHMLLVVPQTTSCNEILNLYSIAMNHILT"[SEQ ID NO:10]
BASE COUNT        477 a     349 c     398 g     497 t
ORIGIN      13 bp upstream of SmaI site.
    1       tcacaaatac cccgggaacc gcggcggcgt gtgcgtgtgg ccgcgtgtgc ggcggcggcg
   61       cgggaggagc cgggagcggc agccggttcg ggcggtggc atcatggacg agaaggtgtt
  121       caccaaggag ctggaccagt ggatcgagca gctgaacgag tgcaagcagc tgtctgagtc
  181       ccaggttaag agcctctgca gaaggctaaa gaaatcctgg acaaaagaat ccaatgtgca
  241       agaagttcga tgtccagtca ctgtccgtgg agatgtgcat gggcaatttc atgatctcat
  301       ggaactgttt agaattggtg gcaaatcacc agatacaaat tacttgttta tggcgatta
  361       tgttgacaga ggatattatt cagtggaaac agttactctg cttgtagctc ttaaggttcg
  421       ttaccgtgaa cgtatcacca ttcttcgagg aaatcatgag agcagacaga tcacacaagt
  481       atatggtttc tacgatgagt gtttaaggaa atacggaaat gcaaatgttt ggaagtattt
  541       tacagacctt tttgactatc ttcctctcac tgccttggtg gatgggcaga tcttctgtct
  601       acatggtggc ctctcaccat ccatagatac actggatcac atcagagcac ttgatcgcct
  661       acaagaagtt cctcatgagg gtccaatgtg tgacttgctg tggtcagatc cagatgaccg
  721       tggagggtgg ggtatatctc ctcgagggc tggttacacc tttgggcagg atatttctga
  781       gacatttaat catgccaatg gcctcacgtt ggtgtctaga gctcatcagc tggtgatgga
  841       gggatataac tggtgccatg accgaaatgt agtaacgatt tcagtgctc caaactattg
  901       ttatcgttgt ggtaaccaag ctgcaatcat ggaacttgat gatactctaa aatactcttt
  961       cttgcagttt gacccagcac ccgcagaggc aagccacatg ttactcgtcg taccccagac
 1021       tacttcctgt aatgaaattt taaacttgta cagtattgcc atgaaccata tattgaccta
 1081       atggatatgg gaagagcaac agtaactcca caagtgtcag agaatagtta acattcaaaa
 1141       aaacttgttt tcacacggac caaaaagatg tgccatataa aaatacaaag cctgtcatca
 1201       acagccgtga ccactttaga atgaaccagt tcattgcatg ctgaagcgac attgttggtc
```

TABLE 6-continued

```
1261      aagaaaccag tttctggcat agcgctattt gtagttactt tgctttctct gagagactgc
1321      agataagatg taaacattaa caccccgtga atacaattta acttccattt agctatagct
1381      ttactcagca tgactgtagg ataagaatag cagcaaacaa tcattggagc ttaatgaaca
1441      tttttaaaaa taagtaccaa ggcctcccct ctacttgtga gttttaaaat cgttttttgtt
1501      tattttcagg gtaccgttta atttaattgt atgatttgtc tcgcatcagt ttattttccc
1561      tctcaaatct agcctcatgt tgttctttgt tactgtcaca acctggtgag ttgtttttgaa
1621      tggaattgtt ttttttttctc cctgctgtaa gatgatgtta ctgcacaaga gcactgcagt
1681      gttttccata ataaacttgt gaactaagag atgaaaaagt c [SEQ ID NO:11]
```

(C2) Suppression of the Protein Phosphatase Regulatory Subunits

As a complementary approach to the one described in Section c.1, the expression of the regulatory subunits of either PP1 (inhibitor-1, inhibitor-2, or DARPP-32) or PP2A can be suppressed by one of the techniques described previously herein. For informational purposes, the DNA sequences of these substances is provided by Table 7 below.

TABLE 7

```
LOCUS       AI139158      481 bp    mRNA          EST        23-SEP-1998
DEFINITION  qc19d12.x1 Soares_fetal_heart_NbHH19W Homo sapiens cDNA clone
            IMAGE:1710071 3' similar to SW:IPP1_HUMAN Q13522 PROTEIN
            PHOSPHATASE INHIBITOR 1;, mRNA sequence.
ACCESSION   AI139158
NID         g3645130
KEYWORDS    EST.
SOURCE      human.
ORGANISM    Homo sapiens
            Eukaryota; Metazoa; Chordata; Vertebrata; Mammalia; Eutheria;
            Primates; Catarrhini; Hominidae; Homo.
REFERENCE   1 (bases 1 to 481)
AUTHORS     NCI-CGAP http://www.ncbi.nlm.nih.gov/ncicgap.
TITLE       National Cancer Institute, Cancer Genome Anatomy Project (CGAP),
            Tumor Gene Index
JOURNAL     Unpublished (1997)
COMMENT
            Contact: Robert Strausberg, Ph.D.
            Tel: (301) 496-1550
            Email: Robert_Strausberg@nih.gov
            This clone is available royalty-free through LLNL; contact the
            IMAGE Consortium (info@image.llnl.gov) for further information.
            Seq primer: -40m13 fwd. ET from Amersham
            High quality sequence stop: 459.
FEATURES             Location/Qualifiers
     source          1 . . . 481
                     /organism="Homo sapiens"
                     /note="Organ: heart; Vector: pT7T3D (Pharmacia) with a
                     modified polylinker; Site_1: Not I; Site_2: Eco RI; 1st
                     strand cDNA was primed with a Not I - oligo(dT) primer [5'
                     TGTTACCAATCTGAAGTGGGAGCGGCCGCATCTTTTTTTTTTTTTTTTTT 3'],
                     [SEQ ID NO:12],
                     double-stranded cDNA was size selected, ligated to Eco RI
                     adapters (Pharmacia), digested with Not I and cloned into
                     the Not I and Eco RI sites of a modified pT7T3 vector
                     (Pharmacia). Library went through one round of
                     normalization to a Cot = 5. Library constructed by
                     M. Fatima Bonaldo. This library was constructed from the
                     same fetus as the fetal lung library, Soares fetal lung
                     NbHL19W."
                     /db_xref="taxon:9606"
                     /clone="IMAGE:1710071"
                     /clone_lib="Soares_fetal_heart_NbHH19W"
                     /sex="unknown"
                     /dev_stage="19 weeks"
                     /lab_host="DH10B (ampicillin resistant)"
BASE COUNT       89 a     123 c     118 g     151 t
ORIGIN
      1     ttgacctaac accaaattta tcactttta aaaacaagag attttcccca aaagtgaagg
     61     aataagaaac aaatccggtg tccatgcatt cccaaactgc agtcttgatc ccaagatacc
    121     tcctcctctc tcagaccgag ttggctccct tggaatccag tggtggtata tgggttgagg
    181     gttcttttgt gctgggttcc ttactgcctc tctcgtgagt tttagggatg cattctgcag
    241     ttttttttgc tgtcccagag gtgcccagcc ttgactccac ttctgtgtct gggatcccag
    301     gtgggcggga ctcctgggtt cctgtgctct cagcggcccc ctcaggttcc tctccttgct
    361     gctgttgccc caggtgatgt tcaaccatca tctggagctc tttcattgtg ggtgtgatcc
    421     ttgtcatctt cttccgttgc cgtggagaca ttgccaaagt ggacttgaga tgtgggttgg
    481     g [SEQ ID NO:13]
LOCUS       AA188560      439 bp    mRNA          EST        10-MAR-1998
DEFINITION  zp78f05.r1 Stratagene HeLa cell s3 937216 Homo sapiens cDNA clone
```

TABLE 7-continued

```
                    626337 5' similar to SW:IPP2 HUMAN_P41236 PROTEIN PHOSPHATASE
                    INHIBITOR 2;, mRNA sequence.
ACCESSION           AA188560
NID                 g1775788
KEYWORDS            EST.
SOURCE              human.
ORGANISM            Homo sapiens
                    Eukaryota; Metazoa; Chordata; Vertebrata; Mammalia; Eutheria;
                    Primates; Catarrhini; Hominidae; Homo.
REFERENCE           1 (bases 1 to 439)
AUTHORS             Hillier, L., Allen, M., Bowles, L., Dubuque, T., Geisel, G., Jost, S.,
                    Krizman, D., Kucaba, T., Lacy, M., Le, N., Lennon, G., Marra, M.,
                    Martin, J., Moore, B., Schellenberg, K., Steptoe, M., Tan, F.,
                    Theising, B., White, Y., Wylie, T., Waterston, R. and Wilson, R.
TITLE               WashU-NCI human EST Project
JOURNAL             Unpublished (1997)
COMMENT
                    Contact: Wilson R K
                    Washington University School of Medicine
                    4444 Forest Park Parkway, Box 8501, St. Louis, MO 63108
                    Tel: 314 286 1800
                    Fax: 314 286 1810
                    Email: est@watson.wustl.edu
                    This clone is available royalty-free through LLNL; contact the
                    IMAGE Consortium (info@image.llnl.gov) for further information.
                    Insert Length: 1296 Std Error: 0.00
                    Seq primer: -28M13 rev2 from Amersham
                    High quality sequence stop: 368.
FEATURES            Location/Qualifiers
     source         1 . . . 439
                    /organism="Homo sapiens"
                    /note="Vector: pBluescript SK-; Site_1: EcoRI; Site_2:
                    XhoI; Cloned unidirectionally. Primer: Oligo dT. HeLa 53
                    epithelioid carcinoma cells grown to semi-confluency
                    without induction. Average insert size: 1.5 kb; Uni-ZAP XR
                    Vector. ~5' adaptor sequence: 5' GAATTCGGCACGAG 3'
                    [SEQ ID NO:14],
                    -3' adaptor sequence: 5' CTCGAGTTTTTTTTTTTTTTTTT 3'"
          [SEQ ID NO:15]
                    /db_xref="GDB:5045035"
                    /db_xref="taxon:9606"
                    /clone="626337"
                    /clone_lib="Stratagene HeLa cell s3 937216"
                    /sex="female"
                    /dev_stage="HeLa S3 cell line"
                    /lab_host="SOLR (kanamycin resistant)"
BASE COUNT       154 a     89 c     112 g     83 t      1 others
ORIGIN
     1      gacttcctct atggtggcgt cggcgaacag ccccgcggga atgtcgacga ggagctgagc
    61      aaaaaatccc agaagtggga tgaaatgaac atcttggcga cgtatcatcc agcagacaaa
   121      gactatggtt taatgaaaat agatgaacca agcactcctt accatagtat gatggggat
   181      gatgaagatg cctgtagtga caccgaggcc acttgaagcc atgcgccag acatctttag
   241      ccaggaaatt agctgcagct gaaggcttgg agccaaagta tcggattcag gaacaagaaa
   301      gcagtggaga ggaggatagt gacctctcac ctgaagaacg agaaaaaaag cgacaatttg
   361      aaatgaaaag gaagcttcac tacaatgaag gactcaatat caaactagcc agacanttaa
   421      tttcaaaaga cctacatga [SEQ ID NO:16]
LOCUS               HSU60823         750 bp    mRNA           PRI       11-JUL-1996
DEFINITION          Human potent heat-stable protein phosphatase 2A inhibitor I1PP2A
                    mRNA, complete cds.
ACCESSION           U60823
NID                 g1408223
KEYWORDS            .
SOURCE              human.
ORGANISM            Homo sapiens
                    Eukaryotae; mitochondrial eukaryotes; Metazoa; Chordata;
                    Vertebrata; Eutheria; Primates; Catarrhini; Hominidae; Homo.
REFERENCE           1 (bases 1 to 750)
AUTHORS             Li, M., Makkinje, A. and Damuni, Z.
TITLE               Molecular identification of I1PP2A, a novel potent heat-stable
                    inhibitor protein of protein phosphatase 2A
JOURNAL             Biochemistry 35 (22), 6998-7002 (1996)
MEDLINE             96240314
REFERENCE           2 (bases 1 to 750)
AUTHORS             Li, M., Makkinje, A. and Damuni, Z.
TITLE               Direct Submission
JOURNAL             Submitted (13-JUN-1996) Cellular & Molecular Physiology
                    Pennsylvania State University College of Medicine, 500 Univeristy
                    Drive, Hershey, PA 17033, USA
FEATURES            Location/Qualifiers
```

TABLE 7-continued

|  |  |
|---|---|
| source | 1 . . . 750<br>/organism="*Homo sapiens*"<br>/db_xref="taxon:9606"<br>/tissue_type="kidney" |
| CDS | 1 . . . 750<br>/codon_start=1<br>/product="potent heat-stable protein phosphatase 2A inhibitor I1PP2A"<br>/db_xref="PID:g1408224"<br>/translation="MEMGRRIHLELRNRTPSDVKELVLDNSRSNEGKLEGLTDEFEEL<br>EFLSTINVGLTSIANLPKLNKLKKLELSDNRVSGGLEVLAEKCPNLTHLNLSGNKIKD<br>LSTIEPLKKLENLKSLDLFNCEVTNLNDYRENVFKLLPQLTYLDGYDRDDKEAPDSDA<br>EGYVEGLDDEEEDEDEEEYDEDAQVVEDEEDEDEEEEGEEEDVSGEEEEDEEGYNDGE<br>VDDEEDEEELGEEERGQKRKREPEDEGEDDD" [SEQ ID NO:17] |
| BASE COUNT | 260 a     130 c     229 g     131 t |
| ORIGIN |  |
| 1 | atggagatgg gcagacggat tcatttagag ctgcggaaca ggacgccctc tgatgtgaaa |
| 61 | gaacttgtcc tggacaacag tcggtcgaat gaaggcaaac tcgaaggcct cacagatgaa |
| 121 | tttgaagaac tggaattctt aagtacaatc aacgtaggcc tcacctcaat cgcaaactta |
| 181 | ccaaagttaa acaaacttaa gaagcttgaa ctaagcgata acagagtctc aggggggcctg |
| 241 | gaagtattgg cagaaaagtg tccgaacctc acgcatctaa atttaagtgg caacaaaatt |
| 301 | aaagacctca gcacaataga gccactgaaa aagttagaaa acctcaagag cttagacctt |
| 361 | ttcaattgcg aggtaaccaa cctgaacgac taccgagaaa atgtgttcaa gctcctcccg |
| 421 | caactcacat atctcgacgg ctatgaccgg gacgacaagg aggccctga ctcggatgct |
| 481 | gagggctacg tggagggcct ggatgatgag gaggaggatg aggatgagga ggagtatgat |
| 541 | gaagatgctc aggtagtgga agacgaggag gacgaggatg aggaggagga aggtgaagag |
| 601 | gaggacgtga gtggagagga ggaggaggat gaagaaggtt ataacgatgg agaggtagat |
| 661 | gacgaggaag atgaagaaga gcttggtgaa gaagaaaggg gtcagaagcg aaaacgagaa |
| 721 | cctgaagatg agggagaaga tgatgactaa [SEQ ID NO:18] |
| LOCUS | BOVDARPP32    1691 bp    mRNA               MAM        15-DEC-1994 |
| DEFINITION | *Bos taurus* (clone pTKD7) dopamine and cyclic AMP-regulated neuronal phosphoprotein (DARPP-32) mRNA, complete cds. |
| ACCESSION | M27444 |
| NID | g602437 |
| KEYWORDS | phosphoprotein. |
| SOURCE | *Bos taurus* calf brain (*caudate nucleus*) cDNA to mRNA. |
| ORGANISM | *Bos taurus*<br>Eukaryotae; mitochondrial eukaryotes; Metazoa; Chordata;<br>Vertebrata; Eutheria; Artiodactyla; Ruminantia; Pecora; Bovoidea;<br>Bovidae; Bovinae; Bos. |
| REFERENCE | 1 (bases 1 to 1691) |
| AUTHORS | Kurihara, T., Lewis, R. M., Eisler, J. and Greengard, P. |
| TITLE | Cloning of cDNA for DARPP-32, a dopamine- and cyclic AMP-regulated neuronal phosphoprotein |
| JOURNAL | J. Neurosci. 8 (2), 508–517 (1988) |
| MEDLINE | 88117716 |
| COMMENT | On Dec. 16, 1994 this sequence version replaced gi:341699. |
| FEATURES | Location/Qualifiers |
| source | 1 . . . 1691<br>/organism="*Bos taurus*"<br>/db_xref="taxon:9913"<br>/dev_stage="calf"<br>/clone="pTKD7"<br>/tissue_type="brain (*caudate nucleus*)" |
| gene | 342 . . . 1680<br>/gene="DARPP-32" |
| CDS | 342 . . . 950<br>/gene="DARPP-32"<br>/note="dopamine and cyclic AMP regulated neuronal protein"<br>/codon_start=1<br>/product="phosphoprotein"<br>/db_xref="PID:g602438"<br>/translation="MDPKDRKKIQFSVPAPPSQLDPRQVEMIRRRRPTPAMLFRLSEH<br>SSPEEEASPHQRASGEGHHLKSKRSNPCAYTPPSLKAVQRIAESHLQSISNLGENQAS<br>EEEDELGELRELGYPREEEEEEEEDEEEEEDSQAEVLKGSRGSAGQKTTYGQGLEGP<br>WERPPPLDGPQRDGSSEDQVEDPALNEPGEEPQRPAHPEPGT" [SEQ ID NO:19] |
| polyA_signal | 1675 . . . 1680<br>/gene="DARPP-32" [SEQ ID NO:20] |
| polyA_site | 1691<br>/gene="DARPP-32" [SEQ ID NO:21] |
| BASE COUNT | 373 a     530 c     493 g     295 t |
| ORIGIN |  |
| 1 | agcgaaacag agacagaggg agactcgcgg agagggagca agggagatag aggaaggttg |
| 61 | gagagacaca gagagagcga gggaaggagg gccagagacc agccccgcga gcccgaggtg |
| 121 | cggcccagg ggaccgggca cccaggagcc ccagagccgc gagcgggccg cccccaccc |
| 181 | ccgcgcgccc tcccctcgcc ggcgggtatt tttatctgtg cgtgaacagc cctccagctc |
| 241 | ctctctgcca cactcaaccc gctgccgccg cggcccggag cagcgcgggg gagcggagcg |
| 301 | ggatcgcagc ccgagacccc acgacgcgcg ccccgcccgc catggacccc aaagaccgca |
| 361 | agaagatcca gttctccgtg cccgcgcccc ccagccagct cgaccccgc caggtggaga |

TABLE 7-continued

```
421    tgatccggcg caggagacca acccctgcca tgctgttccg gctctcagag cactcctcac
481    cagaggagga ggcctcaccc caccagagag cctcaggaga ggggcaccac ctcaagtcga
541    agagatccaa tccttgtgcc tacacacccc cctcgctgaa agccgtccag cgcattgctg
601    agtctcacct gcagtccatc agcaacctgg gtgagaacca ggcctcggag gaggaggatg
661    agctggggga gctgcgggaa ctgggctacc caagagagga agaggaggag gaagaggagg
721    aggatgaaga ggaggaggag gacagccagg cggaagtcct gaagggcagc aggggggtctg
781    ctgggcagaa gacaacttat ggccaaggtc tggagggtcc ctgggagcgc ccgcctcctc
841    tggatgggcc ccagagagac ggaagctctg aggaccaagt ggaagaccca gcattgaatg
901    aacccgggga ggagccacag cgccctgccc accctgagcc tggcacatag gcacccagcc
961    ctgcatctcc tggaaggaag tgggaggaag cattgatgtt ctccagaaac ccattctgtt
1021   cacaccctat tttgtaccct gcttctcact tgctagggct gcggcttctg acttttagaa
1081   gactaaggct ggtctgtgtt tgcttgtctg cccaacttcg ctgatcccag agtccctggg
1141   cacttgctgc ctgatgccta cccctgccag tcattccccc atacacccag caggaggtgg
1201   gatgggagag cttgcattgg gaaatccagt aaatggggga caaagattca tccttcacaa
1261   ttctactccc tagaccctct cccctgggcg taggaaacca cagggcagga ccctaagatc
1321   tggggaaaag ggatactgag aacttgtaag tgcccataga tctttctcca tcccctgggc
1381   aattccaagt catcaccct tcactgcctt ctaccagggc ccagaattca ggcatctttt
1441   ccacggcctc agcttttggt aaatcttccc cttatcacct gctccccagc ctgggtgcct
1501   ggaagatgga ctggcagaga ctgctttgct gcattttatg tgtgctttga tgccaggaat
1561   gccacctagt ataataagtc cttagggggg cacatggtgg gggagccaag ctctccttgt
1621   cctccagctg ctctgtcccc ttcccctctt ccctgactcc cggcctgaac ctgtaataaa
1681   tctttgtaaa t [SEQ ID NO:22]
```

IV. Routes of Administration, Formulations, and Dosages

In general, the compositions and agents described herein for use in the methodology can be administered in any appropriate carrier for oral, topical, or parenteral administration under in-vivo conditions to a living host subject. The compositions can be introduced by any means that brings access to the vascular endothelial cells within the tissues and organs in the host body. The dosage administered will, of course, vary and be dependent upon the age, health, and weight of the intended recipient; the kind of concurrent treatment, if any; the frequency of treatment, and the degree of the therapeutic effect desired.

If the compositions and agents are to be administered topically, they can be admixed in a concentration range in a pharmaceutically inert topical carrier such as a gel, an ointment, a lotion, or a cream and include such carriers as water, glycerol, alcohol, propylene glycol, fatty alcohols, triglycerides, fatty acid esters, or mineral oils. Other topical carriers are represented by liquid petrolatum, isopropyl palmitate and the like. In addition, minerals such as antioxidants, viscosity stabilizers and the like may be added if and when necessary.

If the compositions and agents are to be given parenterally, these compositions will be prepared in sterile form; in multiple or single dose formats; and dispersed in a fluid carrier such as sterile physiological saline, or 5% dextrose solutions commonly used with injectables. In addition, other modes of administration such as perfusion, intravenous injection, and lavage may be advantageously employed as well.

V. Experiments And Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

Experimental Series I

This series of experiments was performed to determine whether the syndecan-4 molecule is itself subject to phosphorylation; and also to determine whether such phosphorylation is affected by the binding of a growth factor (bFGF) to its receptors on the cell surface.

Experimental Procedures

Materials

Calyculin, chelerythrine, PMA, and bFGF were purchased from Sigma. Gö 6976 was purchased from Calbiochem (La Jolla, Calif.). Chelerythrine, PMA, and Gö 6976 were dissolved in $Me_2SO$.

Isolation of Syndecan-4 Core Proteins

NIH 3T3 cells (American Type Culture Collection, Bethesda, Md.) were grown to confluence in 100-mm plates in Dulbecco's modified Eagle's medium (DMEM) containing 10% fetal bovine serum (Life Technologies Inc.) at 37° C. in a 5% $CO_2$ humidified atmosphere. The cells were harvested by scraping in 1 ml of lysis buffer (150 mm NaCl, 20 mM NaF, 20 mM $Na_4P_2O_7$, 5 mM EDTA, 5 mM EGTA, 1 mM $Na_3VO_4$, 1 mM phenylethylsulfonyl fluoride, 1% Triton X-100, 50 mM HEPES, pH 7.4). The lysate was cleared by centrifugation at 9000×g for 30 min. and then subjected to DEAE-chromatography as described by Scworak et al., *J. Biol. Chem.* 269: 21204–21214 (1994)]. The eluates were dialyzed twice against 10 mM $NH_4HCO_8$, 1 mM β-mercaptoethanol and concentrated by evaporation under vacuum. The concentrated samples were resuspended in 50 μl of digestion buffer (50 mM NaCl, 4 mM $CaCl_2$, 20 mM Tris, pH 7.4) and GAG chains were cleaved off the proteoglycan core proteins by 4 h of incubation in a mixture of 0.06 unit of chondroitinase ABC and 1 unit each of heparinases I, II, and III (Sigma) at 37° C.

Radiolabeling of Cultured Cells

Confluent NIH 3T3 cells were washed twice in phosphate-free DMEM and incubated for 24 h at 37° C. in a 5% $CO_2$ humidified atmosphere in phosphate-free DMEM supplemented with 0.5% fetal bovine serum. The cells were washed twice with methionine, phosphate, and serum-free DMEM and incubated for 6 h in the same medium, supplemented with 400 μCi/ml [$^{35}$S]methionine (New England Nuclear, Boston, Mass.). At the onset of the last 2 h of incubation, 500 μCi/ml [$^{32}$P]orthophosphoric acid (New England Nuclear) was added to the medium.

Immunoprecipitation of Cytoplasmic and Ectoplasmic Syndecan-4 Domains

Cells were washed with PBS (137 mL NaCl, 10 mM $Na_2HPO_4$, 3.6 mM KCl, 1.8 mM $KH_2PO_4$, pH 7.4), dissociated by 0.05% trypsin, 0.5 mM EDTA (Life Technologies, Inc.) in PBS for 10 min at 22° C., and sedimented by 2000×g centrifugation at 4° C. for 5 min. The syndecan-4 ectoplasmic domain was immunoprecipitated from 0.5 ml of medium collected before cell trypsinization or from 0.5 ml of supernatant of the latter centrifugation. The cytoplasmic tail was immunoprecipitated from the pellet after a 30-min extraction at 4° C. in 0.5 mil of lysis buffer supplemented with 100 µM leupeptin, 2 µM pepstatin, and 10 nM okadaic acid (Sigma). Total protein concentrations in each fraction were measured by spectrophotometry at 595 nm (DU 640, Beckman, Fullerton, Calif.) of an aliquot developed for 10 min in Protein Assay Dye Reagent (Bio-Rad). Bovine serum albumin (Life Technologies Inc.) was used as standard.

The medium, trypsinization supernatant, and extracted pellet fractions were precleared by adding 30 µl of 1:1 (v/v) slurry of protein G plus/protein A-agarose beads (Calbiochem), and 10 µl of nonimmune rabbit serum (Life Technologies Inc.). After a 2-h incubation at 4° C. in rotating tubes, the beads were sedimented by 5 min, 5000×g centrifugation at 4° C. The cleared samples were supplemented with 40 µl of 1:1 (v/v) slurry of the above beads and 10 µl of rabbit polyclonal antiserum (syndecan-4 ectoplasmic domain-specific antiserum was added to the medium and trypsinization supernatant samples, and cytoplasmic tail-specific antiserum was added to the extracted pellet fraction) and incubated in rotating tubes for 18 h at 4° C. The agarose beads were collected by centrifugation as above, washed three times in heparinase digestion buffer, and resuspended in 40 µl of digestion buffer, and the GAG chains of the bead-attached ectoplasmic domains from the medium and from the trypsinization-supernatant were cleaved as above. The ectoplasmic and cytoplasmic tails were dissociated from the beads by a 10-min incubation in SDS buffer at 95° C., and the beads were sedimented by a 5 min, 13,000×g centrifugation at 4° C.

Electrophoresis, Transfer, Autoradiography and Immunoblotting

Immunoprecipitated, full-length syndecan-4 core proteins were resuspended in Laemmli sample buffer (2% SDS, 10% glycerol), 0.5% P-mercaptoethanol, 0.004% bromphenol blue, 50 mM Tris-HCl, pH 6.8) resolved by SDS-PAGE on a 10% slab gel, and transferred to a polyvinylidene fluoride (PVDF) membrane (Immobilon-P, Millipore, Bedford, Mass.) for 12 h at 25 mA in 150 mM glycine, 20 mM Tris-HCl, and 20% methanol. The ectoplasmic and cytoplasmic syndecan-4 domains were resolved on a 15% slab gel and transferred for 90 min at 20 mA in 150 mM glycine, 20 mM Tris-HCl, and 30% methanol to a low porosity PVDF membrane (Immobilon-P$^{SQ}$, Millipore). Radiolabeled bands detected by exposure to film (XAR, Kodak, Rochester, N.Y.) were excised, and their radioactivity was measured in both the $^{32}$P and $^{35}$S spectra by scintillation counting (LS 6000IC, Beckman, Fullerton, Calif.). In some cases, the same membranes were used for immunoblotting prior to band excision.

After blocking in PBS containing 5% nonfat milk powder for 1 h at 22° C., the membrane was incubated in the same solution supplemented with 1:3000 (v/v) dilution of either ectoplasmic or cytoplasmic tail-specific antiserum for 2 h, washed with PBS, and incubated for 1 h in 5% milk powder-PBS containing 1:2000 diluted goat anti-rabbit IgG conjugated to peroxidase (Vector Laboratories, Burlingame, Calif.). The secondary antibody was detected, after no additional PBS wash, by chemiluminescence (Western Blot, Chemiluminescence Reagent Plus, New England Nuclear). Molecular weights were estimated by comparison with the electrophoretic mobility of standards (Kaleidoscope Prestained Standards, Bio-Rad). Densitometry of digitized images of immunoprobed membranes (ScanJet 4c, Hewlett Packard) was performed using ImageQuant software (Molecular Dynamics, Sunnyvale, Calif.).

Thin-Layer Chromatography

Bands excised from PVDF membranes were hydrolyzed for 75 min in 6 N HCl at 110° C. Solvent was evaporated under vacuum, and the sediment was washed thrice with $H_2O$. The sediment was resuspended in 5 µl of $H_2O$ after the third evaporation, applied to a thin layer cellulose acetate plate (Sigma-Aldrich), and underwent electrophoresis at 1000 V in 5% acetic acid, 0.5% pyridine, pH 3.0. The radiolabeled phosphoamino acids were detected by phospholuminescence (PhosphorImager, Molecular Dynamics). Phosphorylated, unlabeled Ser, Thr, and Tyr (Sigma) were used as standards and were detected by spraying with ninhydrin.

Experiment 1

To determine the presence and extent of phosphorylation of the syndecan-4 cytoplasmic tail, full-length heparan and chondroitin sulfate-carrying core proteins were isolated from serum-starved, $^{32}$P-labeled NIH 3T3 cells. The results are shown by FIGS. 1A and 1B respectively.

Figure 1B:
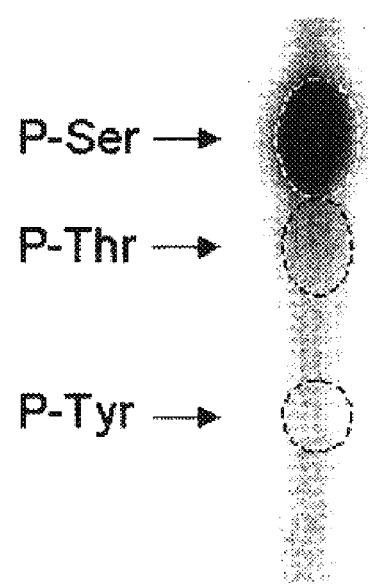

FIG. 1 generally shows the detection of syndecan-4 core protein basal phosphorylation and identification of serine phosphorylation. Lane 1 of FIG. 1A shows an autoradiograph of fibroblast proteoglycans resolved by 10% SDS-PAGE and transferred to a PVDF membrane; lane 2 of FIG. 1A shows a Western immunoblast of the same membrane shown in lane 1. In comparison, FIG. 1B shows a phospholuminescence image of the acid-hydrolyzed, TLC-separated syndecan-4 band (syn-4) shown in FIG. 1. Phosphoamino acids were identified by comparison with the electrophoretic mobility of nonradiolabeled standards: P-Ser, Ser(P); P-Thr, Thr(P); P-Tyr, Tyr(P).

The results of the autoradiography of NIH 3T3 GAG-lysed core proteins is shown in FIG. 1A (lane 1). To identify the syndecan-4 band, the autoradiographed membrane was probed with an antiserum specific to the cytoplasmic tail of the syndecan-4 core protein. The immunoblotting highlighted a single band that ran at an approximate molecular mass of 36 kDa (FIG. 1A, lane 2). A similar syndecan-4 electrophoretic mobility lower than its predicted molecular mass of 20 kDa was observed before with the same antiserum. As illustrated in FIG. 1A, the antiserum-detected band superimposed precisely on the second band from the bottom in the autoradiograph.

Phosphoamino acid analysis of the syndecan-4 band produced a single, intensely labeled spot that corresponded to the electrophoretic mobility of phosphorylated serine as shown by FIG. 1B. The syndecan-4 core protein sequence contains multiple serines [16 in the human syndecan-4 and 15 in the rat]—all but one of which are located in the ectoplasmic domain.

Experiment 2

To determine which domain contains the phosphorylated serine, the susceptibility of the ectoplasmic domain of the syndecans to trypsinization was exploited. Thus the core protein of syndecan-4 was cleaved at the cell surface concurrently with the trypsin dissociation of the $^{32}$P-labeled, adherent cells from the culture plates. The results are visually seen in FIG. 2.

Figure 2A:
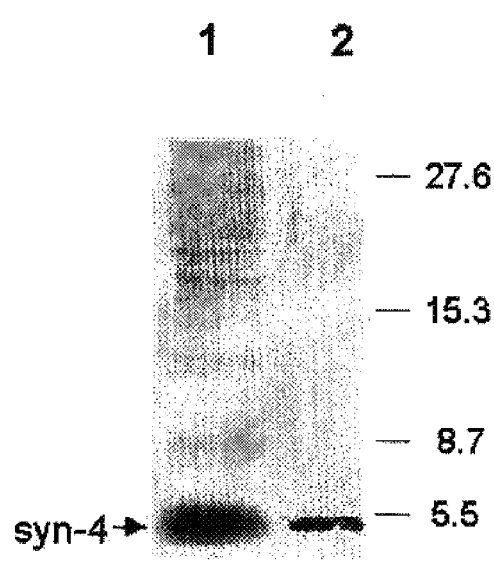
FIGS. 2A and 2B are photographs showing the localization of syndecan-4 core protein phosphorylation to the cytoplasmic tail.
Figure 2B:
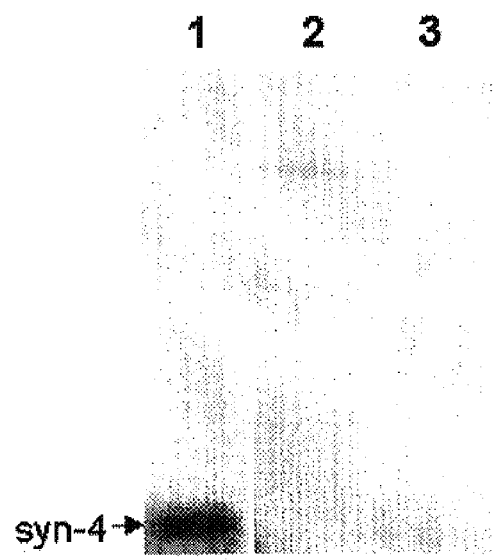

FIG. 2 shows the localization of syndecan-4 core protein phosphorylation to the cytoplasmic tail. Lane 1 of FIG. 2A shows an autoradiograph of Triton X-100 soluble cell fraction immunoprecipitated with syndecan-4 (syn-4) cytoplasmic tail-specific antiserum. Lane 2 of FIG. 2A shows a Western immunoblot of the same membrane shown in lane 1, using syndecan-4 cytoplasmic tail-specific antiserum. Lane 1 FIG. 2B shows Triton X-100 soluble cell fraction immunoprecipitated with syndecan-4 cytoplasmic tail-specific antiserum. Lane 2 of FIG. 2B shows the trypsinized ectoplasmic proteins fraction immunoprecipitated with antiserum specific to the syndecan-4 ectoplasmic domain. Lane 3 of FIG. 2B shows the cell culture medium immunoprecipitated and processed as the sample in lane 2. Autoradiography exposure times were identical for the three samples.

Accordingly, by analogy with syndecan-1, the trypsinization site is most likely between $Arg^{147}$ and $Thr^{148}$ preceding the transmembrane domain. Following trypsinization and detergent extraction, the cleaved syndecan-4 fragment was isolated by immunoprecipitation with the cytoplasmic tail-specific antiserum, which recognizes a 14-residue cytoplasmic sequence. As with the full-length core protein, the $^{32}$P-labeled immunoprecipitate was separated by SDS-PAGE and transferred to a membrane. The band routinely detected in the autoradiographs of these membranes migrated at an approximate molecular mass of 5 kDa, slightly less than the predicted 7-kDa size of the fragment encompassing the trypsinized transmembrane and cytoplasmic tails (FIG. 2A). This lower apparent molecular mass may have resulted from partial degradation during the isolation process or may reflect a higher electrophoretic mobility than the molecular mass standard used for estimating the band size.

To verify the identity of this band, the same membrane was reprobed with the antiserum that recognizes the cytoplasmic tail. The immunoblotted band overlapped the $^{32}$P-labeled one (FIG. 2A), confirming that the latter is comprised of the $Ser^{183}$-phosphorylated cytoplasmic tail of syndecan-4.

To rule out phosphorylation of additional serines in the syndecan-4 core protein outside the cytoplasmic tail, the phosphorylation was examined in three different fractions: (a) the medium, which could contain shed ectoplasmic syndecan-4; (b) the supernatant of the sedimented trypsinized cells, containing the cleaved ectoplasmic domain; and (c) the detergent-soluble fraction extracted from the pellet of the sedimentation, containing the transmembrane and cytoplasmic domains. The ectoplasmic domain of syndecan-4 was immunoprecipitated from the first two fractions with an antiserum specific to this domain; and the third fraction was immunoprecipitated with the cytoplasmic tail-specific antiserum. Autoradiography of the SDS-PAGE-separated fractions revealed a single band in the cytoplasmic fraction lane. No radioactive bands were detected in the lanes of the other two fractions (FIG. 2B). This clearly localizes the phosphorylation to the single serine residue in the cytoplasmic tail of the core protein of syndecan-4.

Experiment 3

To determine the stoichiometry of the basal phosphorylation of syndecan-4, as well as the effect of bFGF and of other compounds on this phosphorylation, the cells were doubly labeled with [$^{35}$S]methionine and [$^{32}$P] orthophosphoric acid. The syndecan-4 carboxyl-terminal proteolytic fragment produced by trypsinization between $Arg^{147}$ and $Thr^{148}$ (referring to the rat sequence numbering) contains a single methionine ($Met^{176}$). Because we have shown above that the phosphorylation of syndecan-4 occurs at a single $Ser^{183}$, the molar ratio of $^{32}P/^{35}S$, as calculated from their specific activities, should be equivalent to the ratio of mol $P_i$/mol syndecan-4, assuming the two radio probes have similar incorporation efficiencies. Because this quantitation method is radiometric, the result is independent of the absolute amounts of protein processed. Using this approach, the stoichiometry of the basal phosphorylation of syndecan-4 in cells starved for 24 h in 0.5% serum, followed by 6 h of serum-free starvation, was 0.31±0.12 (mean±S.D., n=5) of mol $P_i$/mol syndecan-4.

Experiment 4

The participation of the syndecan ectoplasmic domain in bFGF binding raises the question whether this binding is accompanied by intracellular modifications of syndecan-4, such as phosphorylation of its cytoplasmic tail. The results of FIG. 3 reveal the true answer.

Figure 3A:
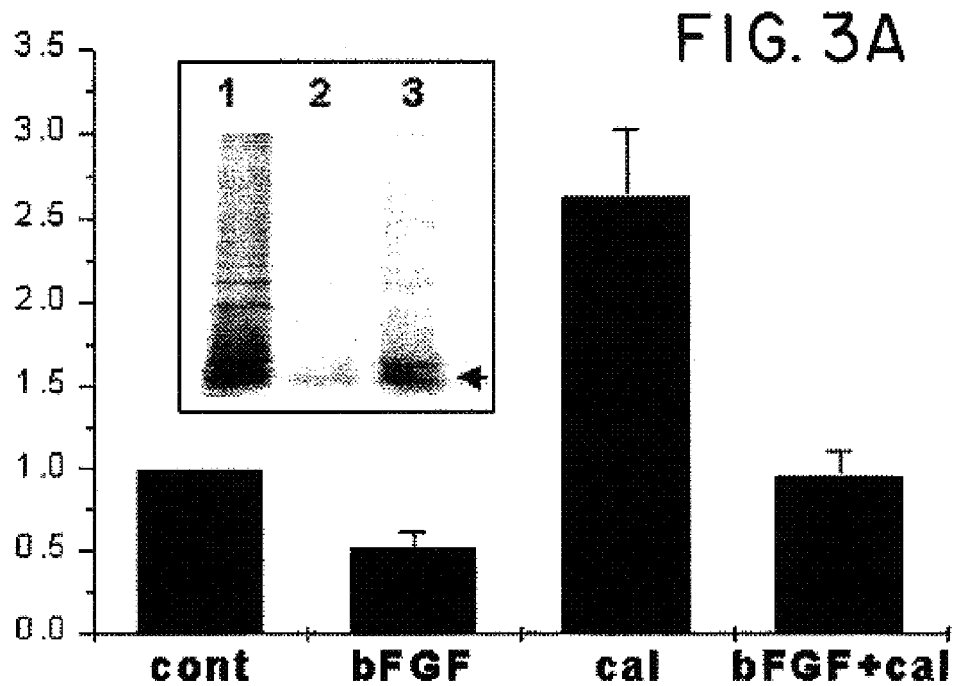
FIGS. 3A and 3B are graphs showing the effects of bFGF and calyculin on syndecan-4 cytoplasmic tail phosphorylation.

FIG. 3 shows the effects of bFGF and calyculin on syndecan-4 cytoplasmic tail phosphorylation. FIG. 3A shows the cumulative results of the effects of bFGF (n=4), calyculin (cal, n=3), and bFGF together with calyculin (bFGF+cal, n=3) on syndecan-4 cytoplasmic tail phosphorylation, relative to untreated control cells (cont). Bars denote standard deviation. The inset shows autoradiographs of cell lysates immunoprecipitated with syndecan-4 cytoplasmic tail-specific antiserum. Lane 1 represents bFGF-untreated cells. Lane 2 represents cells treated with 10 ng/ml bFGF. Lane 3 represents cells treated concurrently with 10 ng/ml bFGF and 5 nM calyculin. Arrow denotes the syndecan-4 band.

Figure 3B:
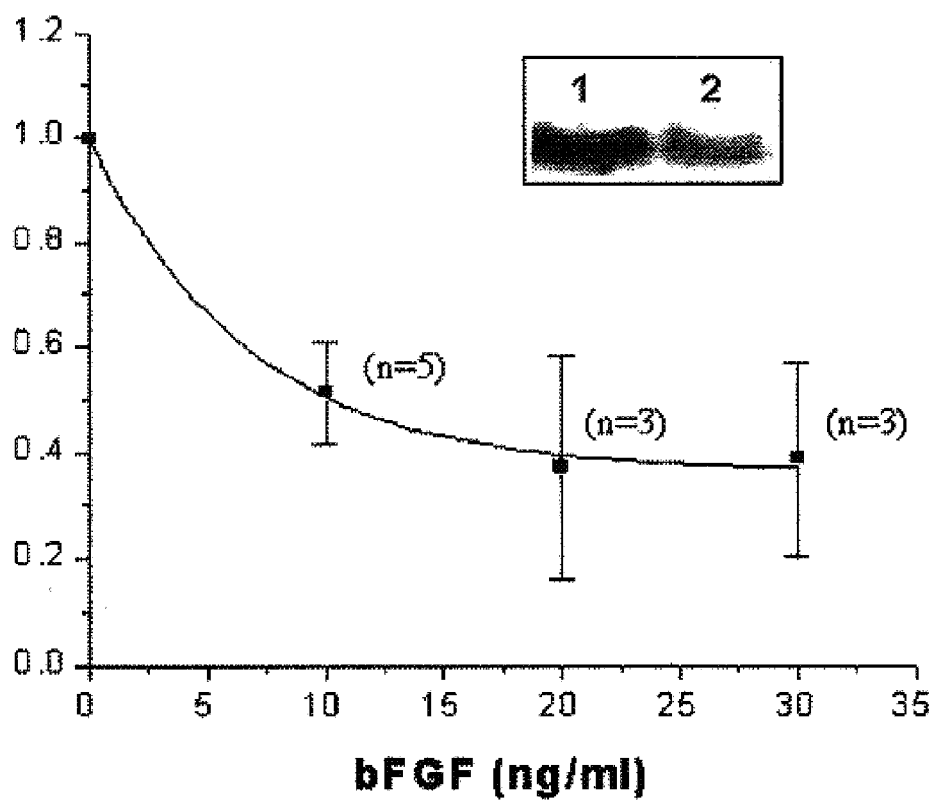

FIG. 3B reveals the dependence of syndecan-4 cytoplasmic tail phosphorylation on bFGF concentration. Phosphorylation stoichiometry was calculated as the ratio of $^{32}P/^{35}S$ counts of the syndecan-4 bands excised from PVDF membranes. Inset shows immunoblotted syndecan-4 bands from control and bFGF-treated (10 ng/ml) cells. Cell lysates containing equal amounts of total protein were applied in each lane.

Experimentally, treatment with 10 ng/ml of bFGF during the last 5 h of the serum-free starvation decreased the phosphorylation stoichiometry of syndecan-4 to 0.16±0.02 (n=5), approximately half its basal level (FIG. 3A). Larger bFGF dosages of 20 and 30 ng/ml further decreased the phosphorylation stoichiometry of syndecan-4 to 0.12±0.06 (n=3), but this decrease was not statistically different from the effect of 10 ng/ml bFGF (FIG. 3B).

To test for the possible involvement of a phosphatase in the bFGF-induced decrease of syndecan-4 phosphorylation, phosphatase 1/2A inhibitor calyculin (5 nM) was applied to bFGF (10 ng/ml)-treated cells. Calyculin countered the effect of bFGF, maintaining the syndecan-4 phosphorylation at its basal level (FIG. 3B). Moreover, when the same calyculin dose was applied to cells in the absence of bFGF, syndecan-4 phosphorylation was increased more than 2.5-fold relative to the basal level.

If, contrary to our assumption, the incorporation efficiency of $^{35}$S is higher than that of $^{32}$P, the bFGF-induced decrease in syndecan-4 phosphorylation could solely result from bFGF up-regulation of syndecan-4 synthesis. To address this possibility, the syndecan-4 expression levels in control and in bFGF-treated cells (processed identically to those in the phosphorylation assays) were compared by immunoblotting cell lysates containing equal amounts of total protein. The syndecan-4 bands, which similar to immunoprecipitated samples (FIG. 2A) ran at an approximate molecular mass of 5 kDa, were detected with the antiserum specific to the ectoplasmic domain; and the amount of protein in each band was quantified by densiometry. In cells treated by 10 and by 30 ng/ml bFGF, the level of syndecan-4 expression was 85% (FIG. 3B, inset) and 93% of the control cells, respectively.

Experiment 5

The possible involvement of PKC in syndecan-4 phosphorylation was then investigated. The experiment data is provided by FIG. 4.

Figure 4A:
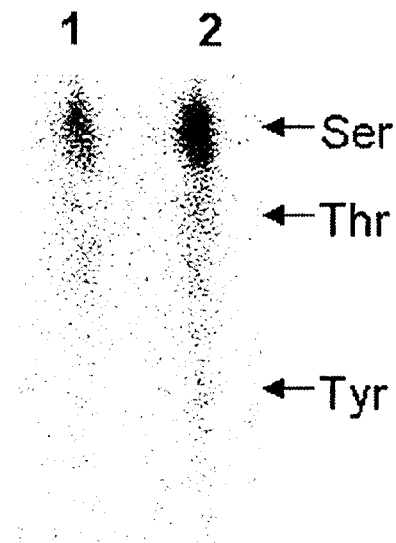
FIGS. 4A–4C are photographs and a graph showing the effects of PKC activation and inhibition on syndecan-4 cytoplasmic tail phosphorylation.
Figure 4B:
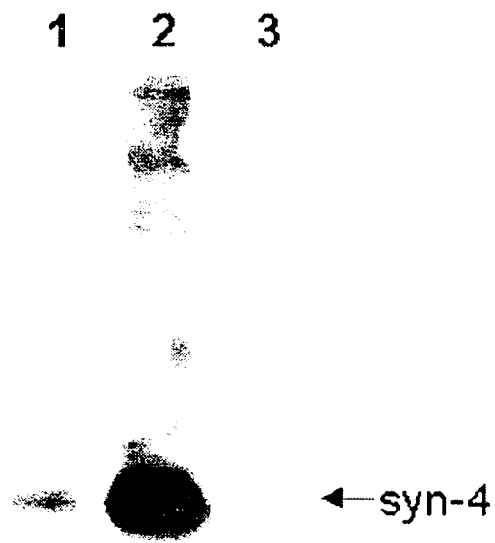
Figure 4C:
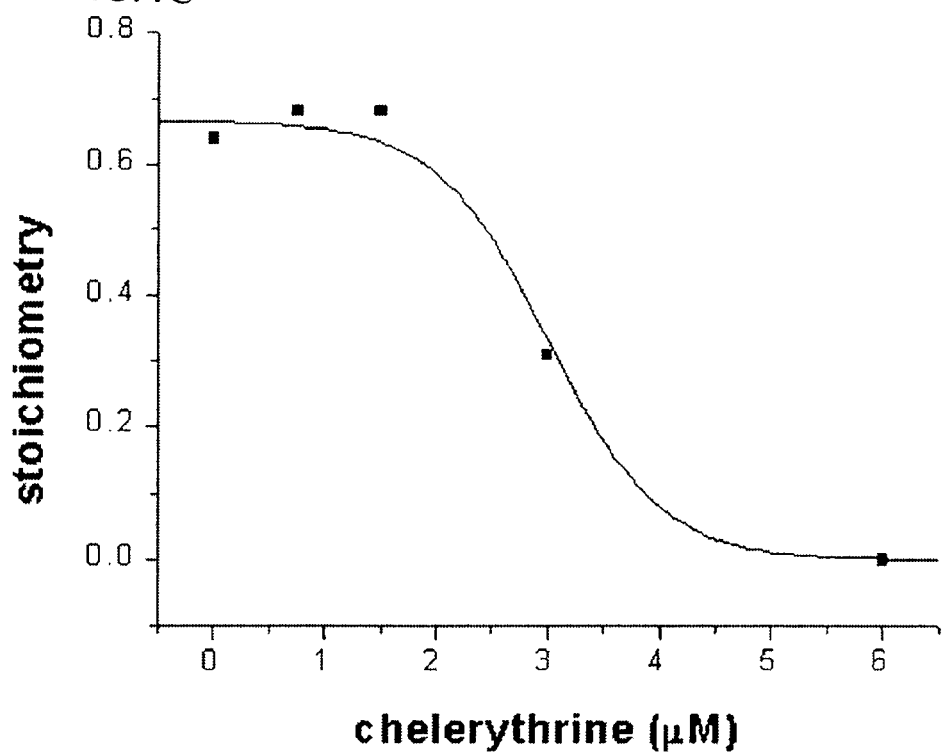

FIG. 4 reveals the effects of PKC activation and inhibition on syndecan-4 cytoplasmic tail phosphorylation. FIG. 4A shows a phospholuminescence image of acid-hydrolyzed, TLC-separated, syndecan-4 (syn-4) bands excised from PVDF membranes of control cells treated by $Me_2$-SO alone (Lane 1) and from cells treated with 0.5 μM PMA (lane 2). FIG. 4B shows autoradiographs of immunoprecipitates from control (lane 1) and PMA-treated cells (lane 2) resolved by SDS-PAGE and transferred to a PVDF membrane. FIG. 4C shows the dependence of syndecan-4 phosphorylation stoichiometry on chelerythrine concentration. Chelerythrine was applied to the cells together with 0.5 μM PMA. These results are representative of two experiments.

Procedurally, to up-regulate PKC, cells were treated with the PKC-activating phorbol ester PMA (0.5 μM) during the last 5 h of the serum-free starvation. This treatment increased only the $Ser^{183}$ phosphorylation of syndecan-4, without having a detectable effect on the phosphorylation of threonine or trypsine residues in the cytoplasmic tail (FIG. 4A). The stoichiometry of the phosphorylation of syndecan-4 in the PMA-treated cells was 0.81±0.33 (n=3), close to 3-fold higher than the basal level. This result indicates that syndecan-4 is either a direct or an indirect PKC substrate.

To further examine the role of PKC in syndecan-4 phosphorylation, the PKC-specific inhibitor chelerythrine was applied to PMA-stimulated cells. The phosphorylation of syndecan-4 started to decline at chelerythrine concentrations above 1.5 μM and was reduced to an undetectable level at 6 μM chelerythrine (FIG. 4, B and C). The latter concentration is less than 10% of the $IC_{50}$ of chelerythrine for the inhibition of protein tryosine kinases. Although supporting the role of PKC in the phosphorylation of syndecan-4, these results do not identify the specific isozyme involved, because both PMA and chelerythrine affect all the four known calcium-dependent cPKCs, as well as the five calcium-independent nPKCs.

To further narrow down the group of possible PKC isozymes, the indolocarbazole Gö 6976, which inhibits calcium-dependent PKC isozymes, was applied to PMA (0.5 μM)-treated cells. The phosphorylation of syndecan-4 was not reduced, however, by Gö 6976 concentrations up to 100 nM, more than 10-fold its $IC_{50}$ for cPKC (data not shown). It is likely, therefore, that the syndecan-4 cytoplasmic tail is phosphorylated by one of the nPKC isozymes.

Conclusions

1. The cytoplasmic tail of syndecan-4 is phosphorylated in cultured fibroblasts and that the extent of its phosphorylation is determined by activities of a nPKC enzyme and a bFGF-activated phosphatase. The phosphorylation site was localized to $Ser^{153}$, immediately upstream of a nine-amino acid segment involved in binding to and activation of PKCα.

2. The experimental series showed a relatively high degree of syndecan-4 phosphorylation in growth-arrested cells, which could be further increased by treatment with PMA or decreased by bFGF. Because $Ser^{183}$ is part of an invariant seven-residue sequence (KKDEGSY), [SEQ ID NO:23], these findings may be relevant to all four members of the syndecan family.

3. The PMA-induced increase in the phosphorylation of syndecan-4 and its decrease by chelerythrine strongly suggest the involvement of PKC in this phosphorylation. In agreement with this observation, we were unable to suppress the PMA-induced phosphorylation of syndecan-4 by a cPKC-specific inhibitor, pointing to the participation of a nPKC isozyme in the phosphorylation.

4. A phosphatase inhibitor reversed the bFGF-induced reduction in syndecan-4 phosphorylation observed in our study. This suggests that bFGF binding up-regulates a phosphatase and/or down-regulates a kinase involved in controlling the level of $Ser^{183}$ phosphorylation.

Experimental Series II

These experiments are directed to investigating the effect of phosphorylation of the cytoplasmic tail of syndecan-4 upon its interaction with phosphatidylinositol 4,5-biphosphate (hereinafter "$PIP_2$") which binds directly to the cytoplasmic tail of syndecan-4 and facilitates its multimerization; as well as its capacity to activate Protein Kinase C α. The involvement of $PIP_2$ for binding and multimerization has been reported previously in the scientific literature [Oh et al., *J. Biol, Chem*. 272: 11805–11811 (1997); Oh et al., *J. Biol. Chem*. 273: 10624–10629 (1998); and Le et al., *J. Biol. Chem*. 273: 13022–13029 (1998)]. However, the functional effects of phosphorylating the cytoplasmic region of the syndecan-4 and its effects on the molecular properties and signaling activity have not yet been elucidated.

Experimental Procedures

Materials

Phosphatidylinositol 4,5-biphosphate ($PIP_2$), phosphatidylserine (PS), and diolein were purchased from Sigma. Recombinant PKCα and PKCδ were synthesized and prepared as described in Nishikawa et al., *J. Biol. Chem*. 272: 952–960 (1997). PKCβ1 optimal substrate peptide (FKLKRKGSFKKFA) [SEQ ID NO:24], was purchased from Tufts University Medical School (Boston, Mass.). A 28 amino acid-long syndecan-4 cytoplasmic tail peptide (S4c) (RMKKKDEGSYDLGKKPIYKKAPTNEFYA) [SEQ ID NO:25], was synthesized by Genemed Synthesis (South San Francisco, Calif.). A similar peptide with a phosphorylated Ser(S4c-P) was synthesized by the Biopolymers Laboratory, Harvard Medical School (Boston, Mass.).

$PIP_2$ Binding Assay $PIP_2$ (from Sigma, dissolved at 2 mg/ml in 20 parts $CHCl_3$, 9 parts MeOH, 1 part $H_2O$, 0.1 part 1N HCl) was dried under $N_2$ and sonicated for 5 min in ice-cold $H_2O$ at a final concentration of 1 mg/ml. Syndecan-4 cytoplasmic tail peptides S4c or S4c-P (100 μM) were incubated on ice for 30 min with the indicated concentrations of $PIP_2$ in 10 mM Tris-HCl (pH 7.5), 75 mM KCl, 0.5 mM DTT, in aliquots of 100 μl. The samples were layered on 30 kDA-molecular-mass cutoff cellulose filters (Ultrafree-MC, Millipore, Bedford, Mass.), and spun at 2000 g for 1 min, following the method described in Haarer et al., *Mol. Cell Biol*. 13: 7864–7873 (1993). The samples (40 μl of each in Laemmli sample buffer, 2% SDS, 10% glycerol, 0.5% β-mercaptoethanol, 0.004% bromophenol blue, 50 mM Tris-HCl, pH 6.8) were resolved by SDS-PAGE on 16.5%

Tris-tricine gels (BioRad Laboratories, Hercules, Calif.). Gels were stained with Coomassie Brilliant Blue G-250 (BioRad Laboratories), and images of the stained bands were digitized (DeskScan II on ScanJet 4c, Hewlett Packard) and quantitated by densitometry (ImageQuant, Molecular Dynamics, Sunnyvale, Calif.).

Size-exclusion Chromatography

Syndecan-4 cytoplasmic tail peptides S4c or S4c-P (300 $\mu$M) were incubated with $PIP_2$ (350 $\mu$M, prepared as above) in 0.5 ml mM HEPES (pH 7.3), 150 mM NaCl, on ice for 30 min. Samples were applied at 4° C. to a Sephadex G-50 (Pharmacia Biotech, Uppsala, Sweden) 30×1.6 cm column equilibrated with the incubation buffer, and the absorbency of the flow through was measured at 280 nm.

Immunoprecipitation

Rat fat pad capillary endothelial cells (RFPEC, gift of Dr. R. D. Rosenberg, MIT (11) were grown to confluence in M199 medium supplemented with 10% FBS (Life Technologies) at 37° C. in a 5% $CO_2$ humidified atmosphere. The cells were harvested by trypsinization, lyzed, and subjected to immunoprecipitation with a cytoplasmic tail-specific antiserum as described previously in Experimental Series I.

Electrophoresis, Transfer, and Immunoblotting

Immunoprecipitated syndecan-4 cytoplasmic tail was re-suspended in Laemmli sample buffer and resolved by SDS-PAGE on a 4–20% Tris-glycine gel (BioRad), and transferred for 2 hrs at 250 mA in 150 mM glycine, 20 mM Tris-HCl, and 20% methanol to a polyvinylidene fluoride (PVDF) membrane (Immobilon-P, Millipore). The membranes were immunoblotted as described previously in Experimental Series I using polyclonal antibodies to PKC$\alpha$ or to PKC$\delta$ (both at 2 $\mu$g/ml; purchased from Santa Cruz Biotechnology, Santa Cruz, Calif.).

Syndecan-4 Cytoplasmic Tail Peptide—PKC Binding Assay

Cytoplasmic tail peptides S4c or S4c-P (10 $\mu$M) were incubated on ice for 30 min either in the presence or absence of $PIP_2$ (20 $\mu$M; prepared as above) with recombinant PKC$\alpha$ (4 $\mu$M) in 0.5 ml of the same buffer used in the $PIP_2$ binding assay. The cytoplasmic tail peptide was immunoprecipitated, and the samples were resolved by SDS-PAGE, transferred, and immunoblotted as described above.

PKC In Vitro Assays

Samples (30 $\mu$l) consisted of PKC$\beta$1 optimal substrate peptide (100 $\mu$M) either with or without syndecan-4 cytoplasmic tail peptides S4c or S4c-P (both at 50 $\mu$M) in 25 mM Tris-HCl (pH 7.4), 5 mL $MgCl_2$, 1 mM DTT, 50 $\mu$M ATP, and 5 $\mu$Ci [y-$^{32}$P]ATP (New England Nuclear, Boston, Mass.). In some assays the buffer was supplemented with either $PIP_2$ (50 $\mu$M), or PS (4 $\mu$g/ml), diolein (6.2 $\mu$g/ml), and 0.2 mM $CaCl_2$. In PKC$\delta$ assays the buffer was supplemented with PS and diolein as above, and with 0.5 mM EGTA. Upon addition of either PKC$\alpha$ (120 ng/ml) or PKC$\delta$ (430 ng/ml), samples were incubated at 30° C. for 10 min, and reactions were stopped by boiling in Laemmli sample buffer for 4 min. The samples were resolved on 16.5% Tris-tricine gels (BioRad Laboratories), transferred to PVDF membranes and detected as described previously in Experimental Series I.

Experiment 6

Syndecan-4 cytoplasmic tail has been shown to activate a mixture of $Ca^{2+}$-dependent PKCs and of recombinant PKC$\alpha$ in the presence of $PIP_2$. To assess the effect of Ser$^{183}$ phosphorylation on syndecan-4-dependent PKC activation, the ability of the 28 amino acid-long syndecan-4 cytoplasmic tail peptide, S4c, and S4c-P peptides to activate recombinant PKC$\alpha$ was studied using the PKC$\beta$1 optimal substrate peptide in an in-vitro assay. The results are graphically illustrated by FIG. 5.

Figure 5:
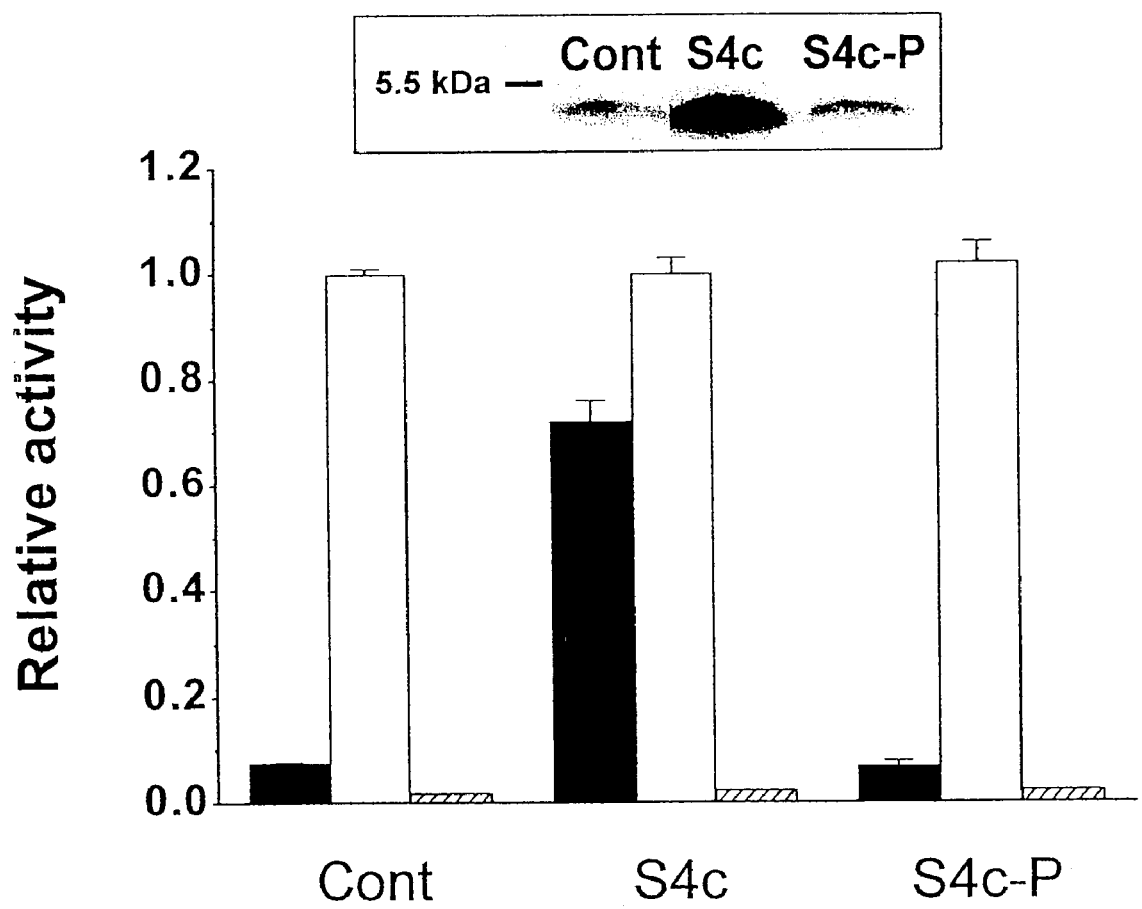
FIG. 5 is a graph with insert showing the activation of PKCα (alpha) isoenzyme by syndecan-4 cytoplasmic tail peptides.

FIG. 5 shows the activation of PKC$\alpha$ cytoplasmic tail peptides. Densitometry histograms of autoradiographic images of PKC $\beta$1 optimal substrate peptide were resolved on 16.5% Tris-tricine gels and then transferred to PVDF membranes (n=3; bars denote SD). The substrate was phosphorylated in-vitro by recombinant PKC$\alpha$ (120 ng/ml) in the presence of PS (4 $\mu$l/ml), diolein (6.2 $\mu$g/ml), and 0.2 mM calcium (white bars), initially without co-factors (striped bars), and then in the presence of 50 $\mu$M $PIP_2$ (black bars). Assays were performed under each set of conditions in the absence (Cont), and in the presence of 50 $\mu$M non-phosphorylated (S4c), or phosphorylated (S4c-P) syndecan-4 cytoplasmic tail peptides. The inset shows autoradiographic images of PKC$\beta$1 optimal substrate peptide phosphorylated in the presence of 50 $\mu$M $PIP_2$.

When the assays were carried out with the standard cPKC cofactors PS, DAG and calcium, the presence of neither the S4c, nor the S4c-P peptides had any additional effect on the catalytic activity of PKC$\alpha$, as shown by FIG. 5. The same result was observed in PKC assays where no cofactors were added. However, the assay conducted in the presence of $PIP_2$, together with the S4c peptide, revealed that the catalytic activity of PKC$\alpha$ towards the PKC$\beta$1 peptide was approximately 10-fold larger than in assays with $PIP_2$ alone. On the other hand, when the S4c-P peptide was added instead of S4c, the phosphorylation level of the substrate was similar to that obtained with $PIP_2$ alone. Unlike PKC$\alpha$, the S4c peptide did not activate PKC$\delta$ under the same conditions (data not shown). The activity of PKC$\alpha$ in the presence of the S4c peptide and $PIP_2$ was 72±10% (±SD, n=3) of its activity in the presence of the S4c peptide, PS, DAG, and calcium.

Experiment 7

The ability of the unphosphorylated but not the phosphorylated cytoplasmic tail of syndecan-4 to activate PKC$\alpha$ in-vitro may relate to a reduced PKC$\alpha$ affinity upon phosphorylation of the cytoplasmic tail. Previous studies [Oh et al., J. Biol. Chem. 272: 8133–8136 (1997)] have demonstrated the ability of the cytoplasmic tail of syndecan-4 to bind PKC; and narrowed the identity of the bound PKC isozyme in-vivo down to a group of four ($\alpha$, $\beta$I, $\alpha$II, $\gamma$, and $\delta$). Though PKC$\alpha$ was shown to bind to the cytoplasmic tail of syndecan-4 in-vitro, the cytoplasmic tail could also bind to and be a substrate of PKC$\delta$. To determine the ability of syndecan-4 to bind PKC$\alpha$ or $\delta$ in-vivo, RFPEC lysates were immunoprecipitated with an antiserum specific to the cytoplasmic tail, and the immunoprecipitants were probed with antibodies specific either to the $\alpha$ or $\delta$ PKC isozymes. The results are shown by FIGS. 6A–6C respectively.

Figure 6A:
FIGS. 6A–6C are photographs showing PKC binding to syndecan-4 cytoplasmic tail peptides.
Figure 6B:
Figure 6C:

FIG. 6 reveals the PKC binding to syndecan-4 cytoplasmic tail peptides. FIG. 6A shows immunoblots of recombinant PKC$\alpha$ (lane 1), and of syndecan-4 cytoplasmic tail immunoprecipitated from RFPEC lysate (lane 2). Samples were resolved on 4–20% Tris-glycine gels, transferred to PVDF membranes, and probed with a polyclonal antibody to PKC$\alpha$. FIG. 6B is similar to FIG. 6A but lane 1 is an immunoblot of recombinant PKC$\delta$, and the membrane was probed with a polyclonal antibody to PKC$\delta$. FIG. 6C shows an immunoblot of recombinant PKC$\alpha$ (4 $\mu$M) incubated with 10 $\mu$M non-phosphorylated (lanes 1,2), or phosphorylated (lanes 3,4) syndecan-4 cytoplasmic tail peptides in the absence (lanes 1,3) or in the presence (lanes 2,4) of 20 $\mu$M PIP$_2$, and immunoprecipitated with antiserum specific to the cytoplasmic tail of syndecan-4.

As shown by FIGS. 6A and 6B respectively, the presence of PKCα but not of PKCδ was detected in the immunoprecipitants. The results clearly evidence these facts.

To analyze the effects of syndecan-4 cytoplasmic tail phosphorylation on its ability to bind PKCα, in-vitro assays with recombinant PKCα and the S4c and S4c-P peptides were then performed. Incubation of PKCα with either peptide produced, however, similar degrees of binding both in the presence and absence of PIP$_2$ (FIG. 6C). It follows, therefore, that PKCα binding is not affected by Ser[183] phosphorylation in the syndecan-4 cytoplasmic tail and thus cannot explain the effect of syndecan-4 phosphorylation on the enzyme's activity.

Experiment 8

Both the oligomerization and PKCα activation capacities of the cytoplasmic tail of syndecan-4 have been reported as depending on the presence of PIP$_2$ [Oh et al., *J. Biol. Chem.* 272: 11805–11811 (1997); Lee et al., *J. Biol. Chem.* 273: 13022–13029 (1998)]. It was of interest, therefore, to determine whether the phosphorylation of Ser[183] in the cytoplasmic tail of syndecan-4 affects the affinity of the tail to PIP$_2$. To this end, the in-vitro binding between PIP$_2$ micelles and S4c or S4c-P peptides was compared using a filtration assay. The filter retains the PIP$_2$ micelle-bound peptide, while the unbound peptide passes through it. The results are illustrated by FIGS. 7A and 7B respectively.

Figure 7A:
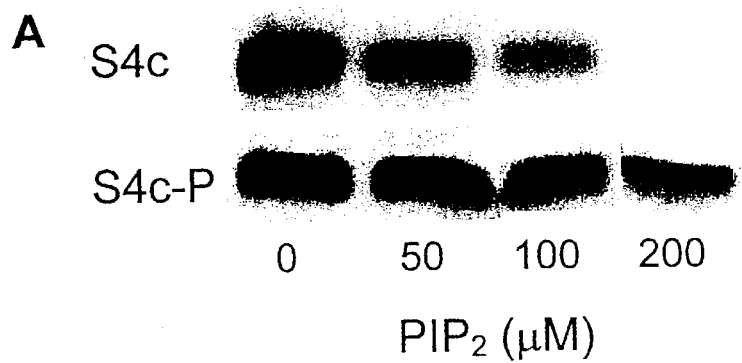
FIGS. 7A and 7B are photographs and a graph showing the binding between $PIP_2$ and syndecan-4 cytoplasmic tail peptides.
Figure 7B:
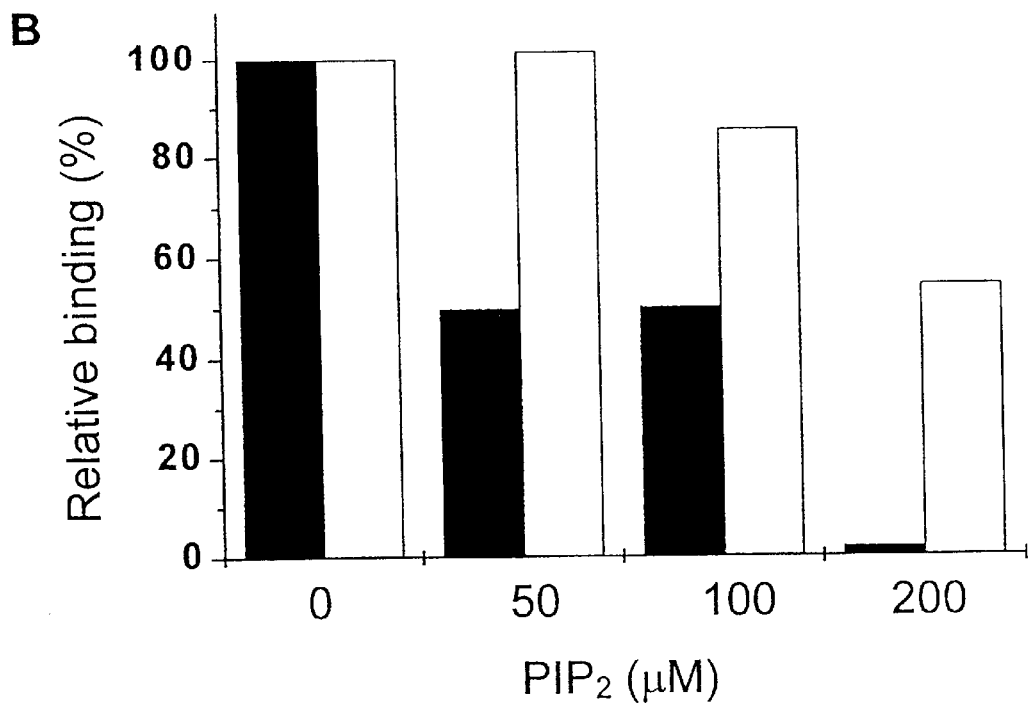

FIG. 7 shows the binding between PIP$_2$ and syndecan-4 cytoplasmic tail peptides. FIG. 7A shows the filter flow-through samples of non-phosphorylated (S4c) and phosphorylated (S4c-P) syndecan-4 cytoplasmic tail peptides, after incubation with PIP$_2$ at the indicated concentrations. Samples were resolved on 16.5% Tris-tricine gels. FIG. 7B graphically illustrates the densitometry results of the gel bands of the S4c (black bars) and S4c-P (white bars) peptides shown in FIG. 7A.

FIG. 7 demonstrates that the binding affinity of the S4c peptide to PIP$_2$, as determined by band densitometry of the SDS-PAGE-resolved filter flow-through samples, was significantly higher than that of the S4c-P peptide. At a peptide:PIP$_2$ molar ratio of 2:1, 50% of the S4c peptide that passed through the filter in the absence of PIP$_2$ was retained, versus none of the S4c-P peptide. Practically all the applied S4c peptide was retained by the filter at a peptide:PIP$_2$ molar ratio of 1:2, while as much as 50% of the S4c-P peptide still passed through the filter under the same conditions. The dissociation constants ($K_d$) calculated from the results shown in FIG. 7 were 2.4 μM for the non-phosphorylated peptide (S4c), vs. 232 uM for the phosphorylated one (S4c-P). Thus, Ser[183] phosphorylation results in significant reduction in the ability of PIP$_2$ to bind to the cytoplasmic tail of syndecan-4.

Experiment 9

Previous studies have demonstrated that the cytoplasmic tail of syndecan-4 undergoes oligomerization in the presence of PIP$_2$; furthermore this oligomerization appeared necessary for PKCα activation. The reduced affinity between the cytoplasmic tail and PIP$_2$ caused by phosphorylation could conceivably be accomplished by changes in the oligomerization properties of syndecan-4. To compare the oligomerization of the S4c peptide to that of the phosphorylated peptide S4c-P, both were incubated either in the presence or absence of PIP$_2$, as described in the Experimental Procedures, and passed through a size exclusion column. The results are graphically represented by FIGS. 8A–8D respectively.

FIG. 8 shows the size-exclusion column chromatography of syndecan-4 cytoplasmic tail peptides. FIGS. 8A and 8C present absorbency profiles at 280 nm of flow-through samples of non-phosphorylated samples; and FIGS. 8B and 8D present phosphorylated syndecan-4 cytoplasmic tail peptides. The samples of FIGS. 8A and 8B were incubated without PIP$_2$; while the samples of FIGS. 8C and 8D contained PIP$_2$. The results shown in FIGS. 8C and 8D are representative of two experiments.

As FIGS. 8A and 8B reveal, both peptides eluted as a single peak when incubated in the absence of PIP$_2$. When the mixtures are incubated in the presence of PIP$_2$, however, the S4c peptide eluted as two peaks—one of an approximate molecular mass of 7 kDa (FIG. 8C), and another heavier peak of a molecular mass greater than 17 kDa (the molecular mass of the heaviest molecular mass standard used in this experiment). The S4c-P peptide, on the other hand, eluted as a single peak of the same approximate molecular mass as the first peak of the S4c peptide (FIG. 8D). These results indicate the cytoplasmic tail of syndecan-4 looses its capacity to form oligomers upon phosphorylation of Ser[183]. Based on the position of the first peaks of the S4c and the S4c-P peptides, it appears that both the S4c and the S4c-P peptides formed dimers, similar to the behavior observed in the PIP$_2$-binding experiment (see FIG. 7). The broader peaks observed with both peptides when incubated in the presence of PIP$_2$, compared with the sharper ones obtained in the absence of PIP$_2$, reflect a wider spread in molecular weight, probably resulting from the range of PIP$_2$ binding to the peptides.

Conclusions

1. This experiment series presents three distinct findings concerning the role of the syndecan-4 core protein in signal transduction: (a) phosphorylation of a single serine residue (Ser[183]) located in the membrane-proximal part of the cytoplasmic tail of syndecan-4 reduces the affinity of the tail to the phosphoinositide PIP$_2$. Upon phosphorylation, the cytoplasmic tail loses its capacity to (b) undergo multimerization and to (c) activate PKCα in the presence of PIP$_2$. These findings provide the first evidence for a functional role of the phosphorylation of Ser[183] in the cytoplasmic tail of syndecan-4.

2. The capacities of the cytoplasmic tail of syndecan-4 to undergo multimerization and to activate PKCα were manifest only in the presence of PIP$_2$. The mechanism of PKCα activation by the cytoplasmic tail of syndecan-4 requires formation of cytoplasmic tail multimers. Ser[183] phosphorylation prevents this oligomerization by inhibiting PIP$_2$ binding to the variable region of the syndecan-4 cytoplasmic tail. It follows, therefore, that the loss of PKCα activation by the cytoplasmic tail upon phosphorylation of Ser[183] is a direct consequence of the concomitant reduction in affinity to PIP$_2$ and impaired multimerization. Since the cytoplasmic tail of syndecan-4 did not activate PKCδ, this activation may be specific to PKCα. On the other hand, Ser[183] phosphorylation had no effect on the capacity of the syndecan-4 cytoplasmic tail to bind PKCα. The ability of syndecan-4 to activate PKCα signaling in endothelial cells, the regulation of this signaling by syndecan-4 phosphorylation, and the previously demonstrated bFGF-dependent regulation of the state of syndecan-4 cytoplasmic tail phosphorylation reveals the existence of a novel bFGF-dependent signaling pathway.

The present invention is not restricted in form nor limited in scope except by the claims appended hereto.

---

What we claim is:

1. A method for stimulating angiogenesis within viable cells, tissues, organs in-situ, said method comprising:

identifying a viable endothelial cell in-situ as a target, said targeted endothelial cell bearing a plurality of transmembrane syndecan-4 proteoglycans positioned at and through the cell surface wherein the 183rd amino acid reside present within the intracellular cytoplasmic domain of said sydecan-4 proteoglycan is a serine residue, administering to said targeted endothelial cell on at least one occasion a predetermined amount of a chemical inhibitor effective against Protein Kinase C δ (delta) isoenzyme activity such that said 183rd serine residue within the cytoplasmic domain of at least some of said syndecan-4 proteoglycans is present in a non-phosphorylated state; and allowing said 183rd serine residue within the cytoplasmic domain of said syndecan-4 proteoglycans to continue to be present in a non-phosphorylated state, whereby a stimulation of angiogenesis in-situ results.

2. The method as recited in claim 1 wherein said chemical inhibitor of Protein Kinase C δ (delta) isoenzyme activity is Chelerythrine.

* * * * *